US011278297B2

(12) United States Patent
Hines et al.

(10) Patent No.: US 11,278,297 B2
(45) Date of Patent: Mar. 22, 2022

(54) HANDHELD SURGICAL INSTRUMENT AND METHOD FOR SUPPLYING TACTILE FEEDBACK TO A USER DURING A KICKBACK EVENT

(71) Applicant: Stryker Corporation, Kalamazoo, MI (US)

(72) Inventors: Douglas Paul Hines, Kalamazoo, MI (US); Rahul Sharma, Gurgaon (IN); Sean Christopher Laughery, Vicksburg, MI (US)

(73) Assignee: Stryker Corporation, Kalamazoo, MI (US)

( * ) Notice: Subject to any disclaimer, the term of this patent is extended or adjusted under 35 U.S.C. 154(b) by 206 days.

(21) Appl. No.: 16/639,604

(22) PCT Filed: Aug. 17, 2018

(86) PCT No.: PCT/IB2018/056238
§ 371 (c)(1),
(2) Date: Feb. 17, 2020

(87) PCT Pub. No.: WO2019/035088
PCT Pub. Date: Feb. 21, 2019

(65) Prior Publication Data
US 2020/0222061 A1 Jul. 16, 2020

Related U.S. Application Data

(60) Provisional application No. 62/546,770, filed on Aug. 17, 2017.

(51) Int. Cl.
*A61B 17/16* (2006.01)
*A61B 90/00* (2016.01)
*A61B 17/00* (2006.01)

(52) U.S. Cl.
CPC ........ *A61B 17/1615* (2013.01); *A61B 17/162* (2013.01); *A61B 17/1626* (2013.01);
(Continued)

(58) Field of Classification Search
CPC . A61B 17/16; A61B 17/1615; A61B 17/1617; A61B 17/162; A61B 17/1622;
(Continued)

(56) References Cited

U.S. PATENT DOCUMENTS

| 4,249,117 A | 2/1981 | Leukhardt et al. |
| 4,267,914 A | 5/1981 | Saar |

(Continued)

FOREIGN PATENT DOCUMENTS

| EP | 2465654 A1 | 6/2012 |
| JP | 2013066943 A | 4/2013 |

(Continued)

OTHER PUBLICATIONS

International Search Report for Application No. PCT/IB2018/056238 dated Dec. 10, 2018, 3 pages.
(Continued)

*Primary Examiner* — Eric S Gibson
(74) *Attorney, Agent, or Firm* — Howard & Howard Attorneys PLLC

(57) ABSTRACT

One embodiment relates to a handheld surgical instrument that comprises a rotary surgical end effector and a coupler configured to cause rotation of the same. The handheld surgical instrument further comprises a motor, which is configured to drive a motor output region. The handheld surgical instrument further comprises a transmission, which defines a transmission input region that interfaces with the motor output region and a transmission output region coupled to the transmission input region. The transmission output region is operably coupled to the coupler, and the
(Continued)

transmission is configured to alter the speed of the coupler relative to the motor output region. The motor output region and the transmission input region interface one another at a motor-transmission interface, and the motor-transmission interface comprises a motor-transmission backlash such that drive of the motor output region within the motor-transmission backlash does not cause rotation of the rotary surgical end effector.

21 Claims, 24 Drawing Sheets

(52) U.S. Cl.
CPC ...... *A61B 17/1628* (2013.01); *A61B 17/1631* (2013.01); *A61B 90/06* (2016.02); *A61B 2017/00734* (2013.01); *A61B 2090/066* (2016.02); *A61B 2562/02* (2013.01)

(58) Field of Classification Search
CPC ............ A61B 17/1624; A61B 17/1626; A61B 17/1628; A61B 17/1631; A61B 17/1633; A61B 17/164; A61B 17/1655; A61B 17/1657; A61B 2090/064; A61B 2090/065; A61B 2090/066; A61B 2562/02
See application file for complete search history.

(56) References Cited

U.S. PATENT DOCUMENTS

| | | | |
|---|---|---|---|
| 5,401,124 A * | 3/1995 | Hettich | B23Q 11/04 173/176 |
| 5,655,412 A | 8/1997 | Luik | |
| 5,747,953 A | 5/1998 | Philipp | |
| 5,914,882 A | 6/1999 | Yeghiazarians | |
| 5,980,248 A | 11/1999 | Kusakabe et al. | |
| 5,984,020 A | 11/1999 | Meyer et al. | |
| 5,993,454 A | 11/1999 | Longo | |
| 6,013,991 A | 1/2000 | Philipp | |
| 6,479,958 B1 * | 11/2002 | Thompson | B25F 5/00 318/430 |
| 6,529,834 B1 * | 3/2003 | Estes | G01C 19/38 702/9 |
| 6,616,446 B1 | 9/2003 | Schmid | |
| 6,960,894 B2 | 11/2005 | Carusillo et al. | |
| 7,395,871 B2 * | 7/2008 | Carrier | B25F 5/00 173/1 |
| 7,410,006 B2 * | 8/2008 | Zhang | B23D 59/001 173/1 |
| 7,497,860 B2 | 3/2009 | Carusillo et al. | |
| 7,552,781 B2 * | 6/2009 | Zhang | B23D 59/001 173/1 |
| 7,638,958 B2 * | 12/2009 | Philipp | A61B 17/32002 318/139 |
| 7,681,659 B2 * | 3/2010 | Zhang | B25B 21/00 173/1 |
| 8,100,912 B2 | 1/2012 | Marietta | |
| 8,316,958 B2 * | 11/2012 | Schell | B25F 5/001 173/178 |
| 8,419,760 B2 | 4/2013 | Wiebe, III | |
| 8,702,710 B2 | 4/2014 | Carusillo | |
| 8,734,153 B2 | 5/2014 | Arzanpour et al. | |
| 8,833,484 B2 * | 9/2014 | Binder | B25F 5/001 173/1 |
| 9,192,394 B2 | 11/2015 | Belagali | |
| 9,193,055 B2 * | 11/2015 | Lim | B25B 21/00 |
| 9,266,178 B2 * | 2/2016 | Eshleman | B25F 5/00 |
| 9,295,476 B2 | 3/2016 | Hassler, Jr. | |
| 9,908,182 B2 * | 3/2018 | Phillips | G05B 19/4083 |
| 10,144,148 B2 * | 12/2018 | Laghate | B27G 19/02 |
| 10,391,563 B2 * | 8/2019 | Schubert | B23B 31/1253 |
| 10,589,413 B2 * | 3/2020 | Goble | G01C 19/08 |
| 10,675,747 B2 * | 6/2020 | Gut | B23Q 11/0092 |
| 2001/0042630 A1 * | 11/2001 | Kristen | B25F 5/00 173/1 |
| 2003/0116332 A1 * | 6/2003 | Nadig | B25D 16/003 173/48 |
| 2004/0211573 A1 * | 10/2004 | Carrier | B25F 5/00 173/2 |
| 2006/0081386 A1 * | 4/2006 | Zhang | B25F 5/00 173/2 |
| 2007/0084613 A1 * | 4/2007 | Zhang | B25F 5/001 173/1 |
| 2009/0065225 A1 * | 3/2009 | Forster | B25F 5/00 173/2 |
| 2012/0036725 A1 | 2/2012 | Osborne et al. | |
| 2012/0184990 A1 | 7/2012 | Twomey | |
| 2012/0318552 A1 | 12/2012 | May | |
| 2013/0099710 A1 * | 4/2013 | Okamoto | A61C 1/06 318/434 |
| 2013/0245704 A1 * | 9/2013 | Koltz | A61B 17/7074 606/86 A |
| 2013/0319710 A1 | 12/2013 | Aoki et al. | |
| 2014/0166323 A1 * | 6/2014 | Cooper | F16P 3/148 173/1 |
| 2014/0216773 A1 * | 8/2014 | Steurer | B23Q 11/0092 173/1 |
| 2014/0231113 A1 * | 8/2014 | Steurer | B25F 5/00 173/1 |
| 2014/0245872 A1 | 9/2014 | George | |
| 2020/0222061 A1 * | 7/2020 | Hines | A61B 17/1631 |
| 2021/0059649 A1 * | 3/2021 | Hunt | A61B 17/1626 |

FOREIGN PATENT DOCUMENTS

| | | |
|---|---|---|
| JP | 2013066948 A | 4/2013 |
| WO | 2007002230 A1 | 1/2007 |
| WO | 2009032314 A1 | 3/2009 |

OTHER PUBLICATIONS

Aghili, F., "Torque Control of Electric Motors Without Using Torque Sensor", Proceedings of the 2007 IEEE/RSJ Internatinal Conference on Intelligent Robots and Systems, San Diego, CA, Oct. 29-Nov. 2, 2007, pp. 3604-3609.

Stryker Instruments, "System 7 Dual Trigger Rotary Handpiece, REF 7205-000-000 Instructions for Use", Rev. C, Apr. 29, 2015, 20 pages.

English language abstract and machine-assisted English translation for JP 2013-066943 extracted from espacenet.com database on Feb. 10, 2020,17 pages.

English language abstract and machine-assisted English translation for JP 2013-066948 extracted from espacenet.com database on Feb. 10, 2020, 19 pages.

* cited by examiner

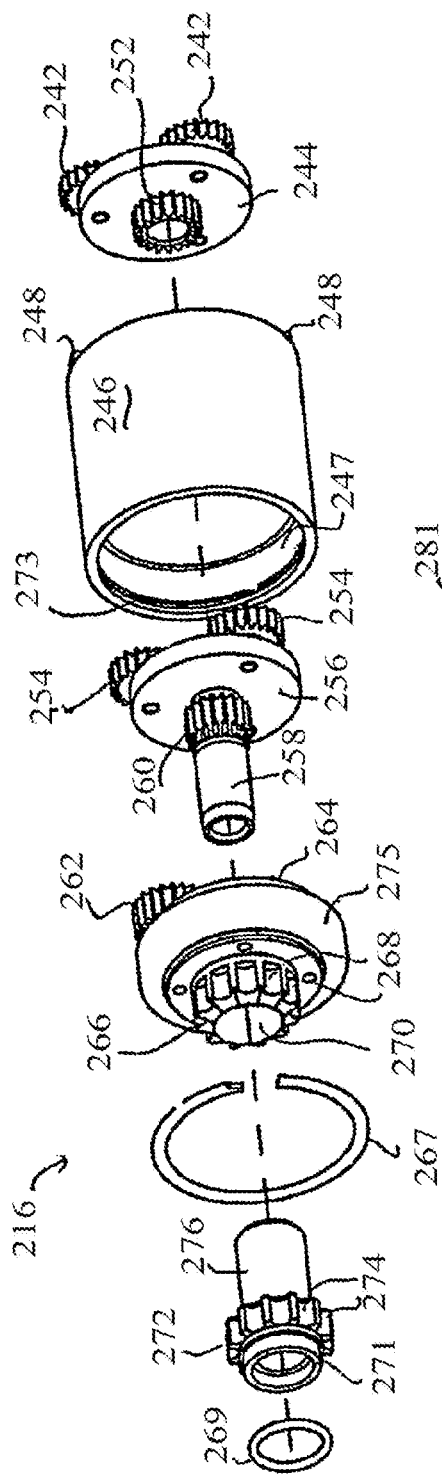
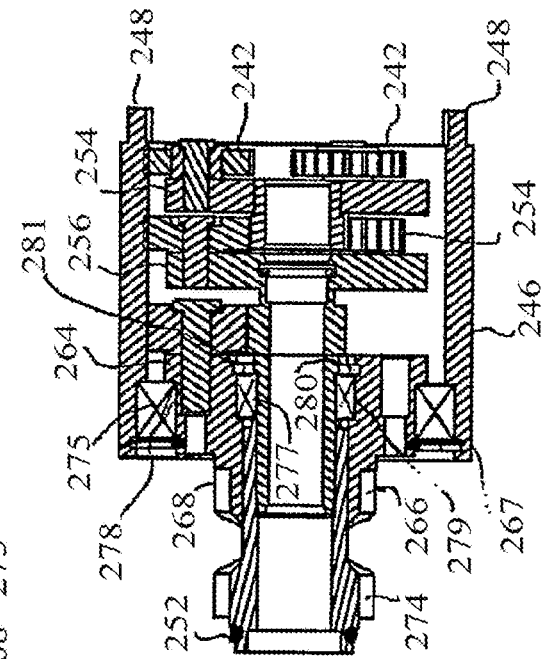
FIG. 8
FIG. 9

HANDHELD SURGICAL INSTRUMENT AND METHOD FOR SUPPLYING TACTILE FEEDBACK TO A USER DURING A KICKBACK EVENT

CROSS REFERENCE TO RELATED APPLICATIONS

This patent application claims priority to and all advantages of International Patent Application No. PCT/IB2018/056238, filed Aug. 17, 2018, which claims benefit to U.S. Provisional Application No. 62/546,770 filed Aug. 17, 2017, which are each hereby incorporated by reference in their entirety.

TECHNICAL FIELD

This disclosure relates to a method and handheld surgical instrument comprising a drive system and a coupler operably engaged with the drive system to perform a feedback function while not performing or terminating an operational function.

SUMMARY OF THE DISCLOSURE

One embodiment relates to a handheld surgical instrument configured to provide tactile feedback in the event of kickback. The handheld surgical instrument comprises a rotary surgical end effector and a coupler configured to operably couple to the rotary surgical end effector to cause rotation of the same. The handheld surgical instrument further comprises a motor, which comprises a motor shaft defining a motor output region. The motor is configured to drive the motor output region. The handheld surgical instrument further comprises a transmission, which defines a transmission input region that interfaces with the motor output region and a transmission output region coupled to the transmission input region. The transmission output region is operably coupled to the coupler, and the transmission is configured to alter the speed of the coupler relative to the motor output region. The motor output region and the transmission input region interface one another at a motor-transmission interface, and the motor-transmission interface comprises a motor-transmission backlash such that drive of the motor output region within the motor-transmission backlash does not cause rotation of the rotary surgical end effector. The handheld surgical instrument further comprises a sensor configured to generate a grip event signal and a controller operably engaged with the sensor to receive the grip event signal from the sensor. The controller is configured to determine a grip event based on the grip event signal, and the controller is further configured to oscillate the motor shaft to perform a feedback function without rotating the rotary surgical end effector.

Another embodiment relates to a handheld surgical instrument configured to provide tactile feedback to a user during a kickback event. The handheld surgical instrument comprises a coupler configured to operably couple to a surgical end effector. The handheld surgical instrument further comprises a drive system, which comprises an output member operably engaged with the coupler for actuating the surgical end effector to perform an operational function. The handheld surgical instrument further comprises a first sensor configured to generate a grip event signal and a controller operably engaged with the first sensor to receive the grip event signal from the first sensor. The controller is configured to determine a grip event based on the grip event signal, and the controller is further configured to oscillate the output member in first and second directions to perform a feedback function while not causing the surgical end effector to perform the operational function.

Still another embodiment relates to a method for providing feedback to a user of a handheld surgical instrument comprising a drive system having backlash, a coupler operably engaged with the drive system, a surgical end effector operably engaged with the coupler to perform an operational function, a first sensor configured to generate at least one grip event signal, and a controller communicating with the first sensor and the drive system. The method comprises the steps of detecting a grip event based on the grip event signal and oscillating the drive system within the backlash without rotating or oscillating the surgical end effector upon detection of the grip event.

BACKGROUND OF THE DISCLOSURE

A common surgical tool used in orthopedic surgery is a surgical drill. The typical surgical drill includes a housing that contains a motor. The surgical drill further includes a coupling assembly that releasably couples a drill bit to the motor so that a surgeon may actuate the motor to rotate the drill bit. As implied by its name, the surgical drill is configured to drill bores in the tissue against which the drill bit is applied. One type of surgical procedure in which it is necessary to drill a bore is a trauma procedure to repair a broken bone.

A disadvantage of the surgical drill is that the drill bit may become suddenly bound, pinched, or misaligned, such that the surgeon may experience kickback in the form of torque being transferred from the drill bit through the handpiece to the surgeon. Debris may impede the rotation of the drill bit, and the kickback can create discomfort for the surgeon and decrease the ability of the surgeon to control the surgical drill, particularly when the surgical drill is used to perform high-speed drilling or high-torque reaming in high-density bone applications.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination within one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings.

FIG. 8 is an exploded view of the transmission of the handheld surgical instrument.

FIG. 9 is a cross sectional view of the transmission of FIG. 8.

DETAILED DESCRIPTION

Figure 1:
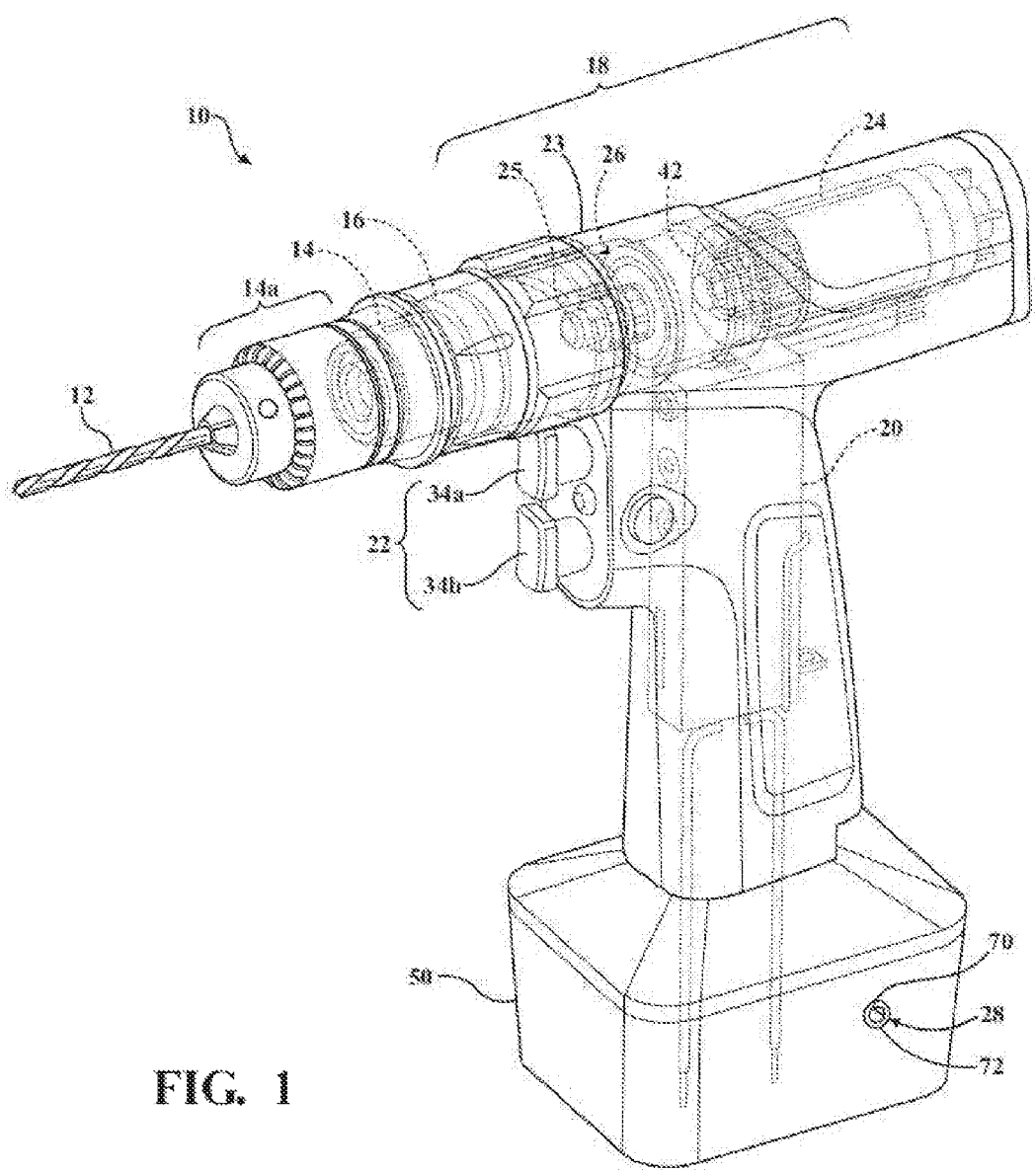
FIG. 1 is a perspective view of a handheld surgical instrument in accordance with one embodiment, with certain internal components illustrated in phantom lines.
Figure 2:
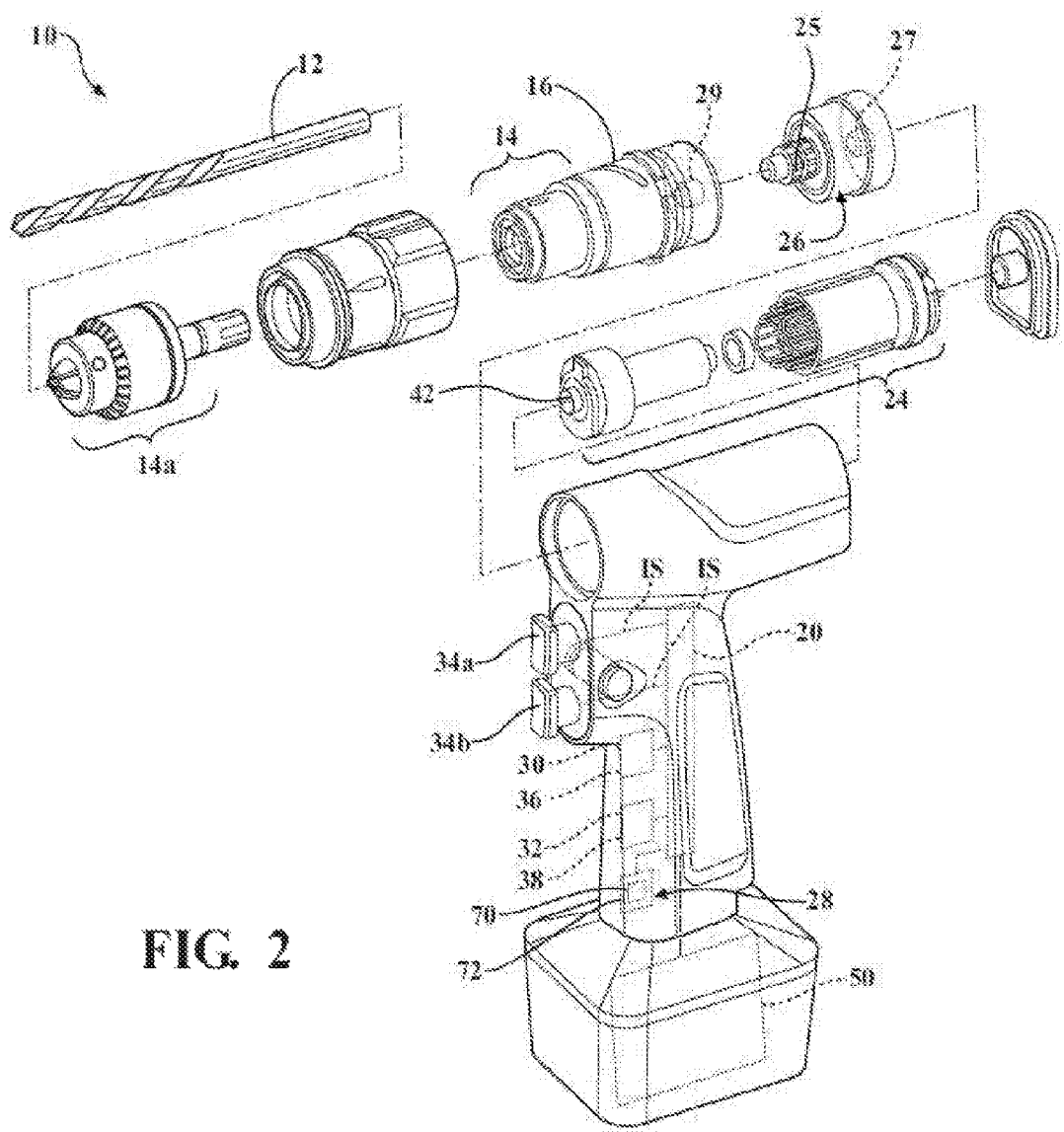
FIG. 2 is an exploded view of handheld surgical instrument of FIG. 1.

Referring to FIGS. 1 and 2, a handheld surgical instrument 10, for use with a surgical end effector 12, is shown for performing an operational function and a feedback function to treat a patient in a health care setting. As described in detail below, the handheld surgical instrument 10 may comprise a coupler 14 and a drive system 18 having a motor 24, transmission 26, and an output member 16 (implemented as a rotary front-end assembly) operably engaged with the coupler 14.

The operational function may be associated with a desired surgical function of the handheld surgical instrument 10. For example, the operational function may be drilling, sawing, cutting, or other functions dependent on the configuration of the handheld surgical instrument 10 and/or the surgical end effector 12. Typically, the operational function referred to herein is rotary cutting.

In this exemplary embodiment, the handheld surgical instrument 10 may be realized as a rotary handpiece, and the associated surgical end effector 12 may comprise a rotary surgical end effector, such as a drill bit. The coupler 14 may be configured to operably couple to the rotary surgical end effector to cause rotation of the same. The coupler 14 may comprise a chuck engaged to the drive system 18, such that the drill bit can be rotated for performing high-speed drilling or high-torque reaming in large bone applications. The coupler 14 can be configured to transmit torque to the surgical end effector 12 in any suitable rotational or linear direction. For example, where the handheld surgical instrument is a drill, the coupler 14 is configured to provide torque to the drill bit.

The rotary handpiece 10 may comprise an output member 16 comprised of, among other things, a spindle that rotates in response to actuation of the motor 24. Attached to the front end of the spindle is the coupler 14. The coupler 14 releasably holds a device to the spindle so that the device rotates in unison with the spindle. Generally, two types of devices are releasably coupled to the output member 16. The first type of device is the actual surgical end effector, for example, the drill bit or the reamer. The surgical end effector may have a shaft, and the proximal end or rear end of the shaft may be releasably held to the output member by the coupler. The second type of device coupled to a rotary handpiece is a front-end attachment, such as a speed-altering surgical attachment. The attachment has a housing with opposed front and rear ends. An input shaft extends from the attachment rear end. The attachment front end has its own output spindle and complementary coupling assembly. Where the attachment is a speed-altering surgical attachment, a gear assembly is located between the input shaft and the output spindle of the speed-altering surgical attachment. The gear assembly contains gears that typically increase the torque/decrease the speed of the rotational motion applied to the attached surgical end effector through the attachment output spindle. The actual surgical end effector is coupled to the attachment spindle. The attachment reduces or increases speed of the rotational moment output by the handpiece that is applied to the surgical end effector. Typically, a speed-altering surgical attachment is used to reduce speed and increase torque of the attached surgical end effector. Another embodiment of the speed-altering surgical attachment increases speed and reduces torque of the attached surgical end effector.

In the case where the handheld surgical instrument is provided with a removable attachment which receives torque from the surgical handpiece, the attachment may define the coupler. For drilling procedures, the attachment may comprise a keyless drill chuck attachment, a keyed drill chuck attachment, a modified trinkle drill attachment, a standard trinkle drill attachment, a bur attachment, or the like. For reaming procedures, the attachment may comprise a modified trinkle reamer attachment, a standard trinkle reamer attachment, a keyed reamer chuck attachment, a reamer attachment, a right angle drive modified trinkle reamer attachment, a right angle drive reamer attachment, or the like. For sawing procedures, the attachment may comprise a sagittal attachment. However, it is contemplated that the attachment can comprise other drilling attachments, reaming attachments, or saw attachments.

The surgical end effectors associated with the attachments, as described above, can comprise: micro burs, wires, pins, reamers, radiolucent drill bits, micro blades, or the like. However, in other embodiments, the surgical end effector can comprise other cutting accessories.

Referring to FIGS. 1 and 2, the coupler 14 is of the type configured to operably couple directly to the surgical end effector 12, and the drive system 18 comprises the output member 16 operably engaged with the coupler 14 for actuating the surgical end effector 12 to perform an operational function. The drive system 18 may be configured to transmit torque through the coupler 14 to the surgical end effector 12 to perform the operational function. As described in detail below, the handheld surgical instrument comprises multiple interfaces between driving members used to drive the surgical end effector to perform the operational function, and movement of those driving members within the cumulative backlash of the interfaces can provide tactile feedback without moving the surgical end effector and performing the operational function.

Figure 3:
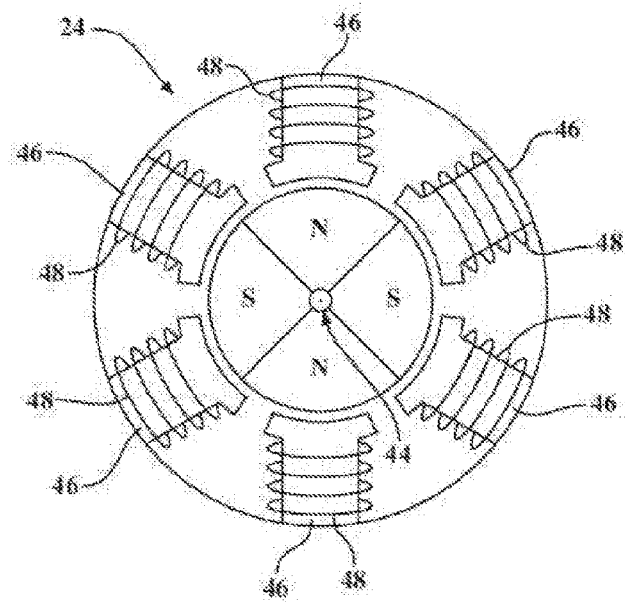
FIG. 3 is a schematic illustration of the motor of FIG. 1, having a rotor oscillating between spaced apart windings to perform the feedback function without commutating the motor or performing the operational function.

The motor 24 comprises a motor shaft that defines a motor output region 42, and the motor 24 may be configured to drive the motor output region 42. The motor 24 may be implemented in the form of an inrunner brushless DC electric motor (BLDC motor) as best shown in FIGS. 2 and 3. The motor output region 42 may be in the form of an output shaft. The BLDC motor 24 can further comprise an external stator 46 with a plurality of windings or coils 48, which are in spaced radial arrangement with the rotor 44. The coils 48 are configured to receive a direct current and become energized to provide electromagnets and create an alternating magnetic field that attracts and repels the permanent magnets of the rotor 44 to generate rotational torque and drive the motor 24 to actuate the surgical end effector 12 to perform the operational function.

It will be appreciated that the drive system can comprise other motors of any suitable type or configuration. For example, the motor could be an outrunner BLDC motor, a brushed electric motor, or any other suitable motor for transmitting torque to the surgical end effector in the rotational direction, a reciprocating linear direction, or any other motion. It will also be appreciated that one motor (not shown) could be used to perform the operational function OF, and a different motor (not shown) could be used to perform the feedback function.

The transmission output region comprises one or more drive heads as detailed in the description for FIG. 8. The output member 16 may be implemented as a rotating front-end assembly that defines an output member input region 29 operably coupled to the transmission output region 25 such that drive of the transmission output region 25 causes drive of the output member input region. The coupler 14 may be implemented as the distal end of the rotating front-end assembly.

The drive system 18 may further comprise a transmission 26 defining a transmission input region 27 operably coupled to the motor output region 42 to cause drive of the transmission input region 27. The transmission 26 further defines a transmission output region 25 operably coupled to the transmission input region 27 such that drive of the transmission input region 27 is configured to cause drive of the transmission output region 25. The transmission output region 25 is operably coupled to the output member 16 such that drive of the transmission output region 25 is configured to cause drive of the output member 16 and alter the speed of said output member 16 relative to said motor 24. The motor output region 42 and the transmission input region 27 interface one another at a motor-transmission interface, and the motor-transmission interface has a motor-transmission backlash such that drive of the motor output region 42 within the motor-transmission backlash does not cause drive of the transmission input region 27.

The transmission 26 comprises a plurality of gears meshed with one another at a plurality of internal transmission interfaces, and at least one of the internal transmission interfaces comprises an internal transmission backlash. In this embodiment, the transmission 26 comprises a planetary gear train that defines a plurality of stages interfacing with one another at a plurality of internal transmission interfaces, and at least one of the internal transmission interfaces comprises an internal transmission backlash such that drive of the transmission within the internal transmission backlash does not cause drive of the output member 16.

The transmission 26 can be configured to increase or reduce the torque output generated by the motor 24 and transmit the torque through the coupler 14 to the surgical end effector 12 or attachment to perform the operational function. In the illustrated embodiment, the transmission 26 is disposed in the distal region 23 of the handheld surgical instrument 10. The handheld surgical instrument 10 may further comprise a clutch, which may be in the form of the clutch 224 illustrated in FIGS. 5B, 6A, and 6B.

Figure 4A:
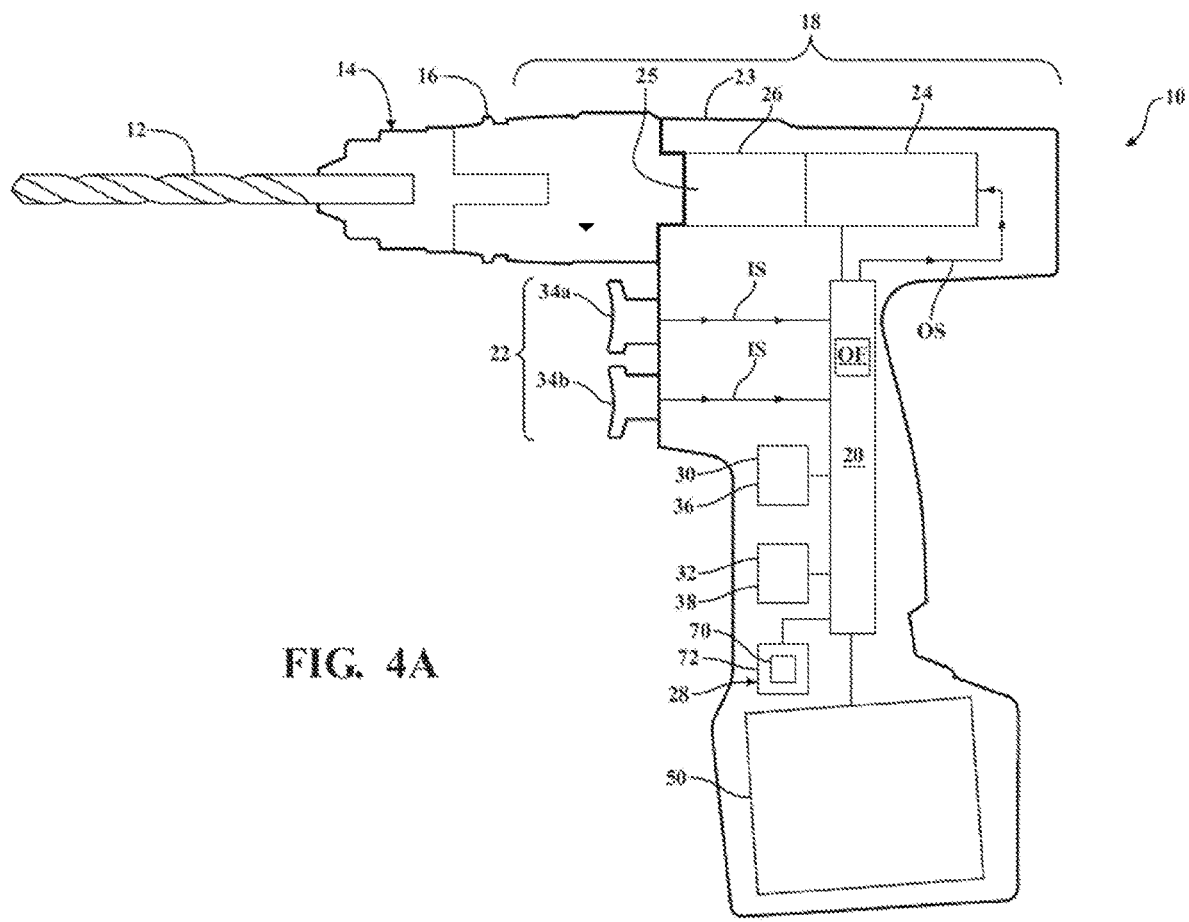
FIG. 4A is a schematic illustration of the handheld surgical instrument of FIG. 1, illustrating the controller receiving an input signal IS from an input device and generating an operate signal to actuate the drive system to transmit torque and speed to the surgical end effector for performing an operational function based on the input signal.

The handheld surgical instrument 10 may further comprise a battery 50 (as shown in FIG. 4A) and/or external power (not shown) to supply energy to the drive system 18, a controller 20, an input device 22, and the like. The drive system 18 can be supplied with a predetermined maximum draw for transmitting torque to the surgical end effector 12 to perform the highest-torque and/or highest speed drilling or reaming associated with the handheld surgical instrument 10. The battery 50 can be lithium-ion battery. However, it is contemplated that the battery 50 can be various other batteries. In one embodiment, a visual indicator 28, such as an LED, may be coupled to the battery 50 as described in detail below. The battery may have a microcontroller that is capable of determining of a status of the battery, such as the state of charge, a level of degradation, a number of uses, etc. The microcontroller of the battery may be configured to trigger the visual indicator based on the status of the battery, such as illuminating the LED when the state of charge or level of wear is below a predetermined threshold.

The input device 22 may comprise first and/or second variable-speed trigger buttons 34a, 34b realized as physical, movable components configured to be depressed, switched, toggled, and the like to generate one or more input signals IS (as shown in FIG. 4A) associated with performing one or more operational functions OF. The first and second variable-speed trigger buttons 34a, 34b, may generate the input signals IS in a way that is proportional to how much the user depresses the first and/or second variable-speed trigger buttons 34a, 34b. Those having ordinary skill in the art will appreciate that the input signal IS could be realized in a number of different ways depending on the specific configuration of the input device 22. For example, the input signal IS could be realized as a variable signal, a digital or analog signal, a waveform, and the like. Thus, as will be appreciated from the subsequent description below, either via the input signal IS directly or by the controller 20, an output signal or waveform used to drive the drive system 18 could affect performance of the operational function in a number of different ways. In other embodiments, the input device can comprise one, three, four, five, or more buttons or other suitable types of input devices.

The handheld surgical instrument 10 can further comprise one or more non-tactile indicators. The non-tactile indicator can comprise an audible indicator, the visual indicator 28, or other suitable indicator mounted in any suitable location or configuration on the handheld surgical instrument 10. In this exemplary embodiment, the visual indicator 28 can comprise a light emitter 70, such as an LED (not shown) and a ring-shaped light guide 72 coupled to the battery. It is contemplated that the handheld surgical instrument may comprise any number of other suitable visual indicators mounted to any location of the handheld surgical instrument, such as the handle or proximal portion of handheld surgical instrument. In other embodiments, the handheld surgical instrument may not comprise visual indicators.

Figure 4B:
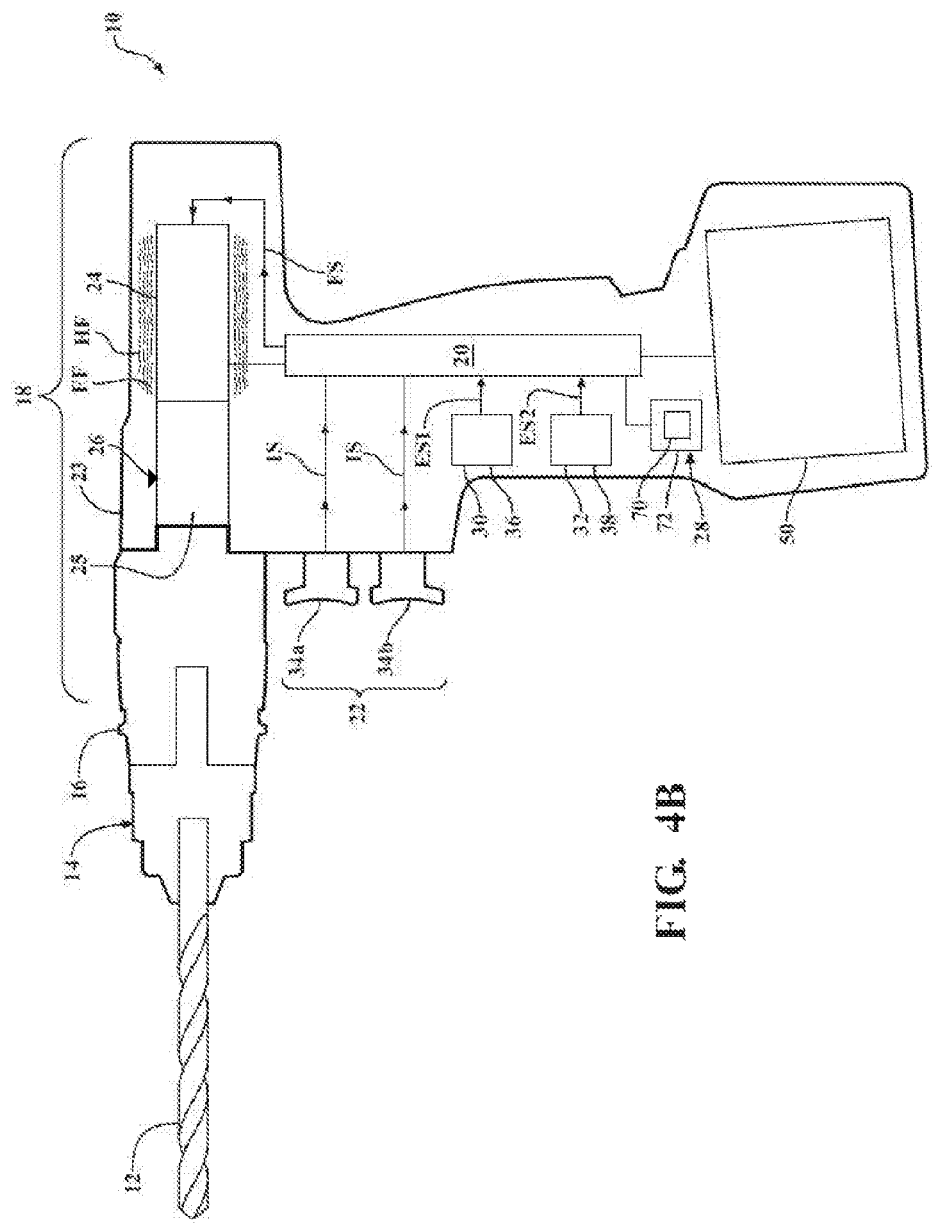
FIG. 4B is a schematic illustration of the handheld surgical instrument of FIG. 1, illustrating the controller receiving first and second event signals from first and second sensors and generating a feedback signal to actuate a motor for performing a feedback function based on the first and second grip event signals.
Figure 4C:
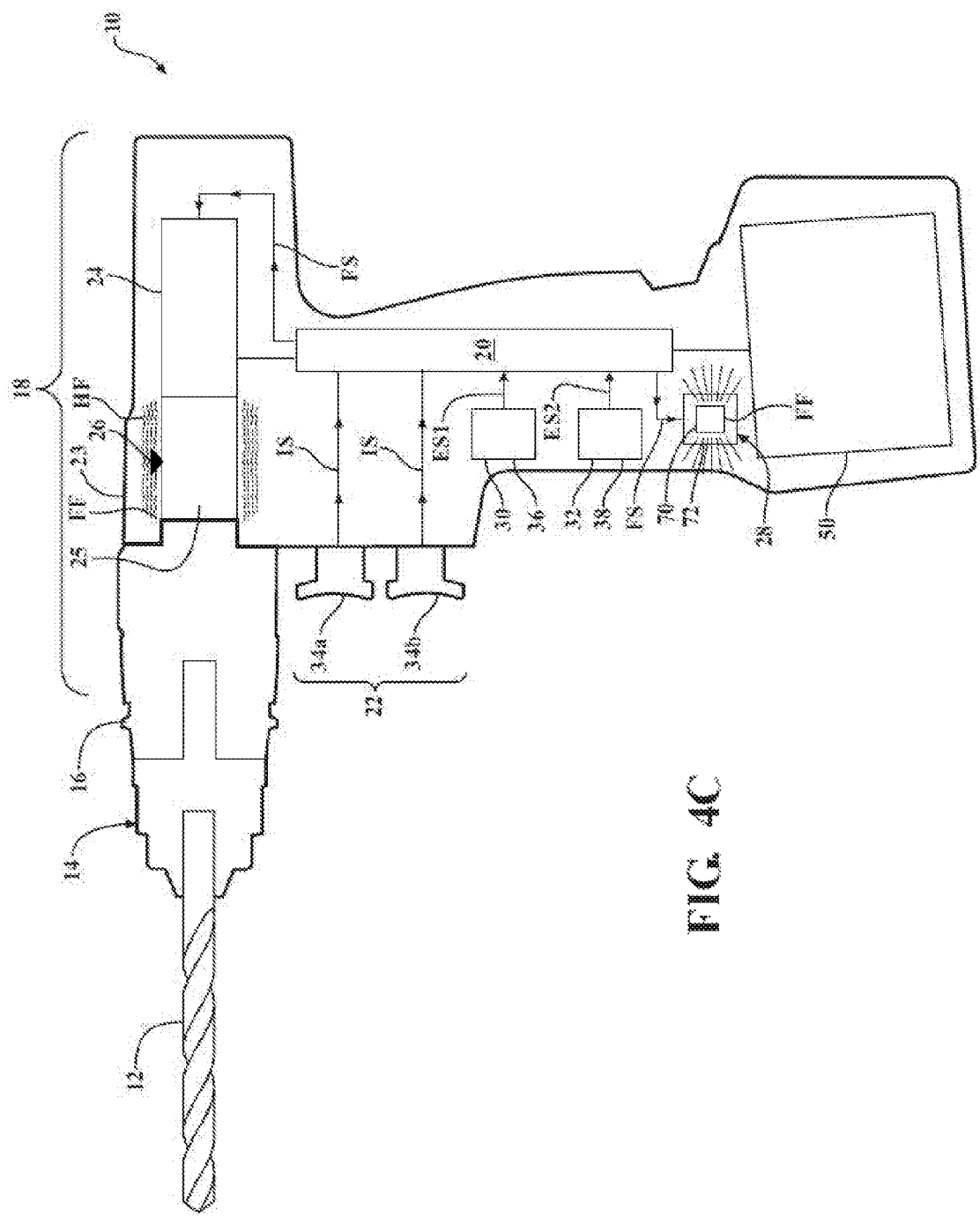
FIG. 4C is a schematic illustration of the handheld surgical instrument of FIG. 1, illustrating the controller receiving first and second grip event signals from first and second sensors and generating a feedback signal to actuate a visual indicator and either the motor or a gear train for performing a feedback function based on the first and second grip event signals.

The handheld surgical instrument 10 can further comprise one or more sensors configured to detect any number of conditions associated with an event and generate a grip event signal. In this exemplary embodiment, the event is a grip event when the surgical end effector 12 becomes bound, pinched, or misaligned while the surgical end effector is being actuated for performing an operational function such that debris impedes the motion of the surgical end effector and kickback transfers torque from the surgical end effector through the transmission and the motor to the user. For example, the grip event may comprise the surgical end effector becoming bound, pinched, or misaligned when drilling into high-density bone such that debris impedes the rotation or other cutting motion of the surgical end effector 12 and the kickback can create discomfort for the user and decrease the ability of the user to control the handheld surgical instrument 10. The handheld surgical instrument 10, can comprise first and second sensors 30, 32 configured to detect two conditions associated with an event and generate first and second event signals ES1, ES2 (as shown in FIGS. 4B and 4C) indicative of those conditions, as described in greater detail below.

In this exemplary embodiment, the first sensor 30 may comprise a gyroscope 36 configured to detect rotation of the handheld surgical instrument 10 at an angular velocity and generate a first event signal ES1 associated with the same. The second sensor 32 can comprise a current sensor 38, which is configured to detect a current supplied to the drive system 18 to actuate the drive system 18 to transmit torque to the surgical end effector 12 for performing the operational function, and the current sensor 38 can generate a second event signal ES2 associated with the same. It is contemplated that the handheld surgical instrument can comprise one, three, four, five or more sensors. The handheld surgical instrument can comprise other suitable sensors configured to detect conditions associated with a low battery level, drive system slippage, or any other event. The detection of a grip event, i.e., a kickback event, can be accomplished in any suitable way, and the hardware and methods of detecting a kickback event described in U.S. Pat. No. 7,681,659, POWER TOOL ANTI-KICKBACK SYSTEM WITH ROTATIONAL RATE SENSOR issued Mar. 23, 2010 and incorporated herein by reference in its entirety.

Figure 5A:
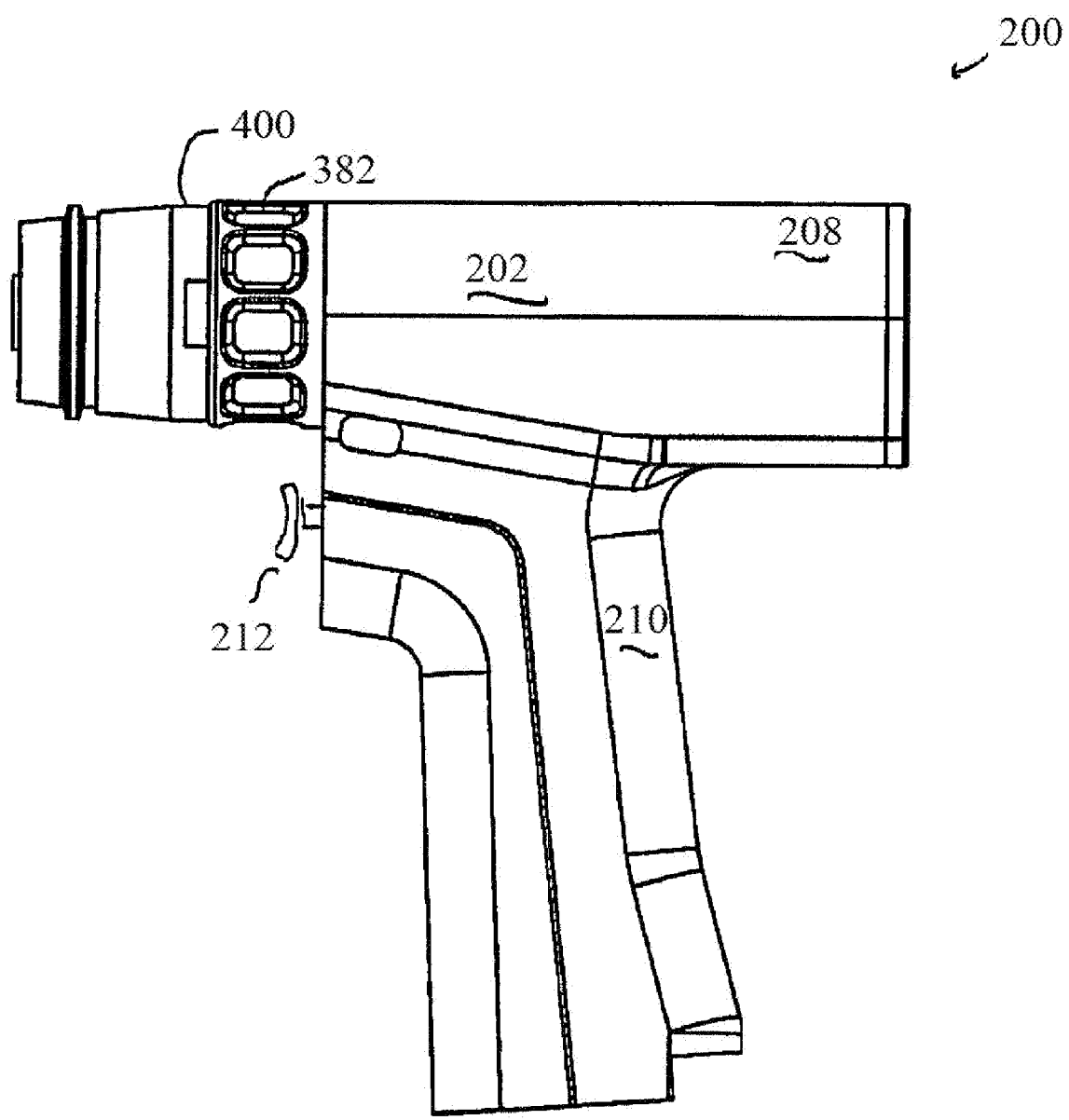
FIG. 5A is a side view of a handheld surgical instrument.
Figure 5B:
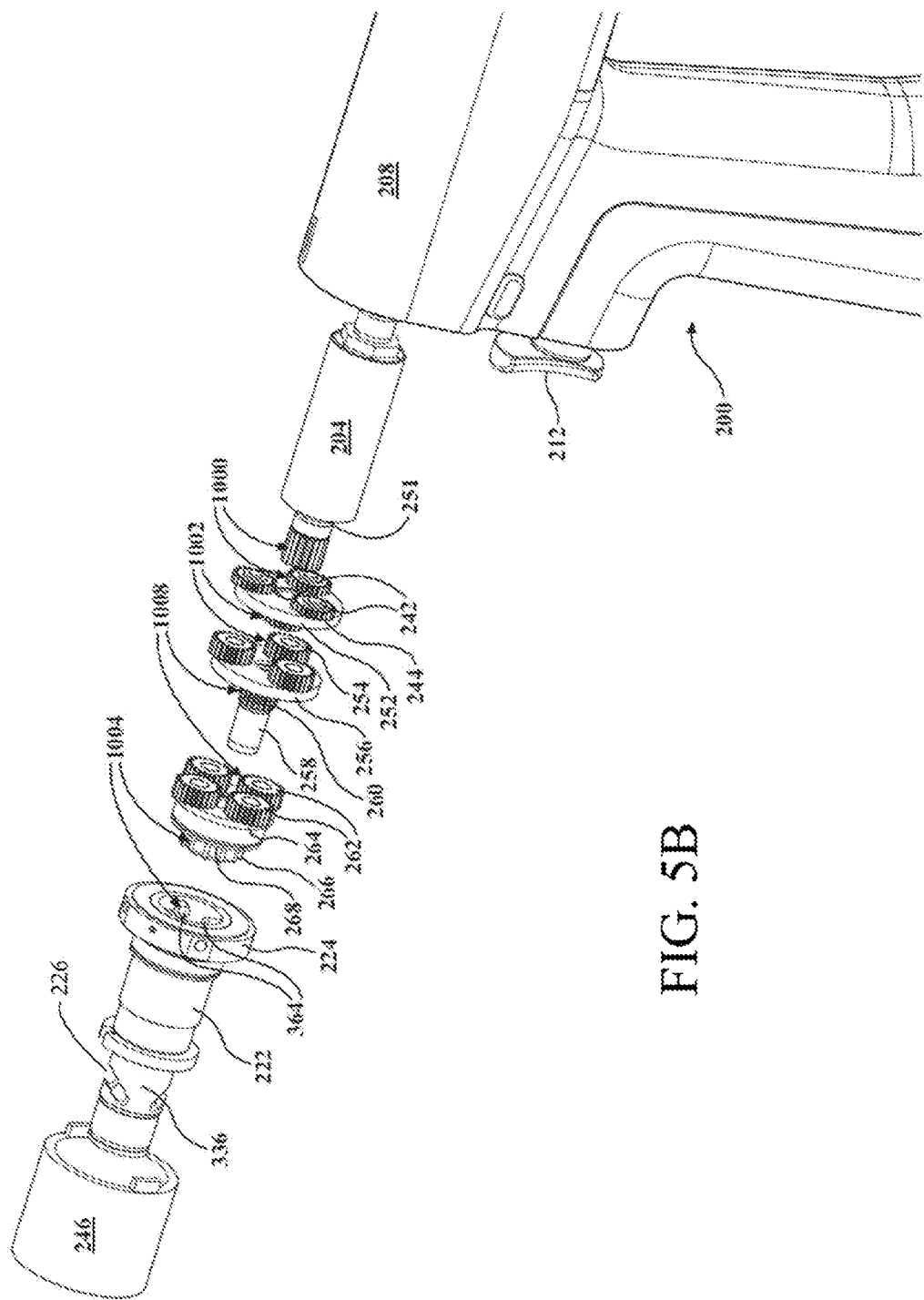
FIG. 5B is a partially exploded view of the handheld surgical instrument of FIG. 5A, illustrating multiple stages of a transmission and multiple interfaces with backlash.

As described in detail below, the controller 20 is operably engaged with each sensor to receive a grip event signal from each sensor, and the controller 20 is configured to determine a grip event based on the same. The controller 20 is further configured to oscillate the drive system 18 in first and second directions within a cumulative backlash of the handheld surgical instrument to perform a feedback function without causing the surgical end effector 12 to perform the operational function. As shown in FIG. 5B, the cumulative backlash may include backlash at the motor-transmission interface 1000, backlash at interfaces between driving members integral to the motor 24, backlash at interfaces 1002, 1008 between gears of the transmission 26, and backlash at a transmission-output member interface 1004. As shown in FIG. 5B, in embodiments where the handheld surgical instrument includes a clutch, the cumulative backlash may include backlash at a transmission-clutch interface 1004 (FIG. 28A).

In one embodiment, the controller 20 may be configured to control the current supplied to the coils 48 and oscillate the motor shaft 42 of the drive system to perform the feedback function without rotating the rotary surgical end effector 12. The controller 20 may be configured to control the current supplied to the coils 48 for selectively commutating any portion of the motor 24, the transmission 60, the clutch, the output member 16, or other suitable portions of the handheld surgical instrument within respective backlashes at interfaces between those components of the handheld surgical instrument or within backlashes internal to the components to perform a feedback function, while not moving the surgical end effector 12 and performing the operational function.

For example, the current supplied to the coils 48 can be insufficient to create a magnetic flux for fully commutating the motor 24 and performing the operational function, but the current may be sufficient to only partially commutate the motor 24 and perform the feedback function. When the motor 24 performs the feedback function, the rotor 44 can oscillate back-and-forth in first and second directions between spaced apart coils 48, thereby causing the BLDC motor 24 to "vibrate" to generate haptic feedback FB without applying sufficient torque and rotational movement through the drive system to the coupler 14 and moving the surgical end effector 12. Depending on the frequency at which the rotor 44 vibrates, the resulting feedback generated by the rotor 44 could be audible feedback and/or haptic feedback.

Continuing the previous example, the rotor 44 can be configured to vibrate at different predetermined frequencies, durations, and the like to generate different types of haptic feedback. Those having ordinary skill in the art will appreciate that audible feedback occurs within a range of frequencies which are detectable by the human ear. Moreover, it will be appreciated that oscillation of the drive system, such as vibration of the rotor 44 can simultaneously generate both audible feedback and haptic feedback of different intensities. For example, feedback FB generated by the rotor 44 could be haptic feedback realized as vibrations translated to and felt by the user at the hand grip or handle of the handheld surgical instrument 10 as described in greater detail below, and also as audible feedback realized as a relatively quiet hum or buzzing noise. Conversely, feedback generated by the rotor 44 could be audible feedback realized as a relatively loud tone, and also as haptic feedback realized as vibrations translated to but not necessarily felt by the user at the input device 22.

The motor output region 42 and the transmission input region 27 interface one another at a motor-transmission interface, which may be implemented as the motor-transmission interface 1000 shown in FIG. 5B. The motor-transmission interface 1000 may have a motor-transmission backlash such that drive of the motor output region 42 within the motor-transmission backlash may perform the feedback function and provide tactile feedback while not causing rotation of the rotary surgical end effector 12 to perform the operational function.

Referring to FIG. 4A, the controller 20 is in electrical communication with the input device 22 to receive the input signal IS from the input device 22. Based on the input signal IS, the controller 20 can determine an operational function OF commanded by the user, and the controller 20 may generate an operate signal OS associated with the operational function OF. The drive system 18 can receive the operate signal OS from the controller 20 and supply sufficient current to the coils to fully commutate the motor 24 and transmit torque through the coupler 14 to the surgical end effector 12 to perform the associated operational function OF.

The input device 22 may comprise the first and second variable-speed trigger buttons 34a, 34b. The first variable-speed trigger button 34a may be fully depressed without depressing the second variable-speed trigger button 34b, such that the input device 22 generates an associated input signal IS received by the controller 20. Based on the input signal IS, the controller 20 may determine that the operational function OF commanded by the user is the highest-speed and/or highest-torque for drilling or reaming in a first direction, and the controller 20 may generate an operate signal OS based on the input signal IS. Conversely, when the second variable-speed trigger button 34b is fully depressed without depressing the first variable-speed trigger button 34a, the input device 22 may generate another input signal IS received by the controller 20. Based on this input signal IS, the controller 20 may determine that the operational function OF commanded by the user is the highest-speed and/or highest-torque drilling or reaming in a second direction that is opposite to the first direction, and the controller 20 may generate the associated operate signal OS. It is contemplated that one or both buttons 34a, 34b can be only partially depressed to generate other input signals IS, and based on these input signals IS, the controller 20 may determine that the operational function OF commanded by the user is less than the highest-speed and/or highest-torque drilling or reaming. In other embodiments, the controller 20 can determine any number of other operational functions OF commanded by the user for the associated handheld surgical instrument 10 and the controller 20 may generate the associated operate signal OS based on the input signal IS. The drive system 18 can receive the operate signal OS from the controller 20, such that the drive system 18 is actuated to transmit torque through the coupler 14 to the surgical end effector 12 for performing the associated operational function OF.

Referring to FIGS. 4B and 4C, the controller 20 can be in further electrical communication with the sensors 30, 32 to receive the event signals ES1, ES2 from the sensors 30, 32 and generate a feedback signal FS based on the event signals ES1, ES2. Continuing with the previous example, the sensors 30, 32 may comprise the gyroscope 36 and the current sensor 38 configured to generate the first and second event signals ES1, ES2 respectively associated with the measured angular velocity of the handheld surgical instrument 10 and the current supplied from the battery to the motor 24.

Based on the first event signal ES1, the controller 20 may determine that the handheld surgical instrument 10 is being rotated at a threshold angular velocity of at least 500 degrees per second. It is contemplated that the controller can determine that the threshold angular velocity associated with the grip event can be above or below 500 degrees per second. In other embodiments, the controller 20 can determine that the grip event has occurred when the gyroscope 36 measures an angular velocity equal to a first threshold angular velocity, and the controller 20 can determine that the grip event has terminated when the gyroscope measures an angular velocity equal to a second threshold angular velocity different from the first threshold angular velocity.

Based on the second event signal ES2, the controller 20 may determine that current is being supplied from the battery 50 to the drive system 18. Because the current sensor 38 generates the second event signal ES2 for indicating rotation or other cutting motion of the surgical end effector 12 associated with a grip event, the current sensor 38 can be used in combination with the gyroscope 36 to prevent the false detection of a grip event. In particular, if the gyroscope 36 were acting alone without the assistance of the current sensor 38, the gyroscope 36 could falsely detect a grip event when the handheld surgical instrument 10, is merely waved in the air at the predetermined angular velocity associated with a grip event, without the input device 22, e.g., button, being actuated to supply power from the battery to the drive system 18 for rotating the surgical end effector 12 and thus creating the possibility of a grip event. In view of these determinations, the controller 20 may further determine that a grip event has occurred and generate a feedback signal FS.

Referring to FIG. 4B, the controller 20 may generate the feedback signal FS to actuate the drive system 18 to perform the feedback function FF, without actuating the drive system 18 to generate torque transmitted to the surgical end effector 12 for performing the operational function OF. In particular, when the controller 20 simultaneously receives the input signal IS and the first and second event signals ES1, ES2 associated with the predetermined event, the controller 20 does not generate the operate signal OS. Rather, the controller 20 may generate only the feedback signal FS to actuate the drive system 18 to perform the feedback function FF and terminate the operational function OF. The operational function OF can be terminated by stopping the drive system 18. For example, a brake device (not shown) may be utilized to slow or at least momentarily halt motion of the drive system 18 when the controller 20 determines that a grip event has occurred based on the first and second event signals ES1, ES2 from the first and second sensors 30, 32.

While the operate signal OS could comprise any suitable configuration sufficient to actuate the drive system 18 to generate torque to perform the associated operational function OF, the feedback signal FS does not actuate the drive system 18 to generate the torque needed to perform the operational function OF. Put another way, the controller 20 is configured to actuate the drive system 18 to generate torque transmitted to the surgical end effector 12 for performing an operational function OF (see FIG. 4A) and independently actuate the drive system 18 to perform one or more feedback functions FF (see FIGS. 4B and 4C). Continuing the previous non-limiting example, the operate signal OS may be associated with the highest-torque and/or highest-speed drilling and reaming associated with the handheld surgical instrument 10. This operate signal OS can require that the drive system 18 be supplied with a maximum draw from the battery 50 or other electrical source for transmitting the necessary torque to the surgical end effector to perform the highest-torque and highest-speed drilling and reaming associated with the handheld surgical instrument 10. The feedback signal FS can require that the drive system 18 be supplied with a draw from the battery 50 that is one-tenth of the maximum available draw from the battery 50 or other electrical source. It is contemplated that feedback signal FS can require that the drive system 18 be supplied with a draw more or less than one-tenth of the maximum available draw from the battery 50 or other electrical source.

The drive system 18 may be configured to perform the feedback function FF to provide feedback to the user by oscillating the rotor 44 in first and second directions, when the drive system 18 receives the feedback signal FS from the controller 20, such that the drive system 18 vibrates the handheld surgical instrument 10 to provide haptic feedback. The haptic feedback can indicate to the user that the grip event occurred and the controller 20 terminated the operational function OF to protect the user, the patient, and the handheld surgical instrument. In addition, the haptic feedback can indicate to the user that the operational function OF did not end as a result of a low or discharged battery or any damage to the handheld surgical instrument 10.

Continuing with the previous example, the drive system 18 can perform the feedback function FF in response to receiving the feedback signal FS from the controller 20. While the operate signal OS could commutate the motor 24 to fully rotate the rotor and subsequently drive the motor 24 to generate rotational torque transmitted to the surgical end effector 12 to perform the operational function OF, the feedback signal FS can be insufficient to fully commutate the motor 24 in the same manner. The feedback signal can be sufficient to vibrate the motor 24 to generate haptic feedback HF and perform the feedback function FF for reasons other than the grip event.

The controller 20 may be configured to control the drive system 18 to generate haptic feedback HF that can be used to indicate a status condition to the user. By way of non-limiting example, haptic feedback HF could be used to indicate the grip event while also verifying proper functionality of the drive system 18 and charge status of a battery 50, such as may be advantageously implemented in connection with a diagnostics and/or service mode of the handheld surgical instrument 10. In one embodiment, the controller 20 may be configured to generate a plurality of different haptic waveforms, which may be used to perform the feedback function FF by vibrating the drive system 18 at different frequencies, durations, intensities, and the like, so as to generate correspondingly different haptic feedback HF. The specific type of haptic feedback HF generated by the drive system 18 could be used to provide the user with a number of different types of tactile feedback FB and, thus, could advantageously afford the handheld surgical instrument 10 with enhanced functionality in use. By way of illustration, haptic feedback HF could be implemented as a short "burst" of vibration directed toward the user so as to indicate activation of the input device 22 during a grip event when the operational function of the drive system is terminated. For example, the controller can implement the feedback function FF for the same amount of time that the user actuates the input device 22, e.g., button, for generating the input signal. However, the duration of the feedback function FF can be longer or shorter than the time that the input device 22 is actuated by the user.

Referring to FIG. 4C, the controller 20 can further transmit the feedback signal FS to non-tactile indicators. In this non-limiting example, the controller 20 can transmit the feedback signal FS to the visual indicator 28 to actuate the visual indicator 28 to provide feedback FB when the controller 20 determines an event based on the first and second event signals ES1, ES2. Where the visual indicator 28 comprises the light emitter 70 and/or the ring-shaped light guide 72, the feedback signal FS can actuate the light emitter 70 to emit a constant light through the entire ring-shaped light guide 72 or a portion of the same. However, the feedback signal FS can actuate the light emitter 70 to intermittently emit light at regular or irregular predetermined frequencies. The feedback signal FS may actuate the light emitter to emit one or more colors indicating feedback associated with the event. For example, the feedback signal FS may actuate the light emitter to intermittently emit a red light to indicate a kickback or grip event, intermittently emit a yellow light to indicate slippage of the drive train 18, or continuously emit a solid red light to indicate a low battery. It is contemplated that the controller 20 can generate other feedback signals FS to actuate the light emitter to emit any color at any frequency, actuate other visual indicators having other configurations, or actuate other non-tactile indicators to provide any type of feedback FB to the user.

The controller 20 may have one or more microprocessors for processing instructions or for processing an algorithm stored in memory to control operation of the drive system 18 and/or generation of the input signal IS, the feedback signal FS and/or the operate signal OS, such as via the drive system 18. Additionally or alternatively, the controller 20 may comprise one or more microcontrollers, field programmable gate arrays, systems on a chip, discrete circuitry, and/or other suitable hardware, software, or firmware that is capable of carrying out the operational and feedback functions OF, FF described herein.

The controller 20 may generate the operate signal OS and the feedback signal FS in the form of separate waveforms or output signals. The operate signal OS and the feedback signal FS may be pulse-width modulation signals. However, these signals could be of any suitable type or configuration sufficient to drive the drive system 18 for performing the operational function and oscillate the drive system 18 for performing the feedback function FF and provide feedback FB as noted above.

FIGS. 5A, 5B, 6A and 6B illustrate a rotary handheld surgical instrument 200 constructed in accordance with one embodiment. It should be appreciated that other constructions are also possible. Handheld surgical instrument 200 has a housing 202 in which in a motor 204 is seated. In one embodiment of the handheld surgical instrument 200, motor 204 is a DC motor. In other embodiments, motor 204 may be an AC motor, or a pneumatic or hydraulically driven motor. Integral with the motor 204 is rotating output shaft in the motor output region 206. Handheld surgical instrument housing 202 is shaped to have a generally cylindrical head 208 in which motor 204 is fitted.

Figure 7:
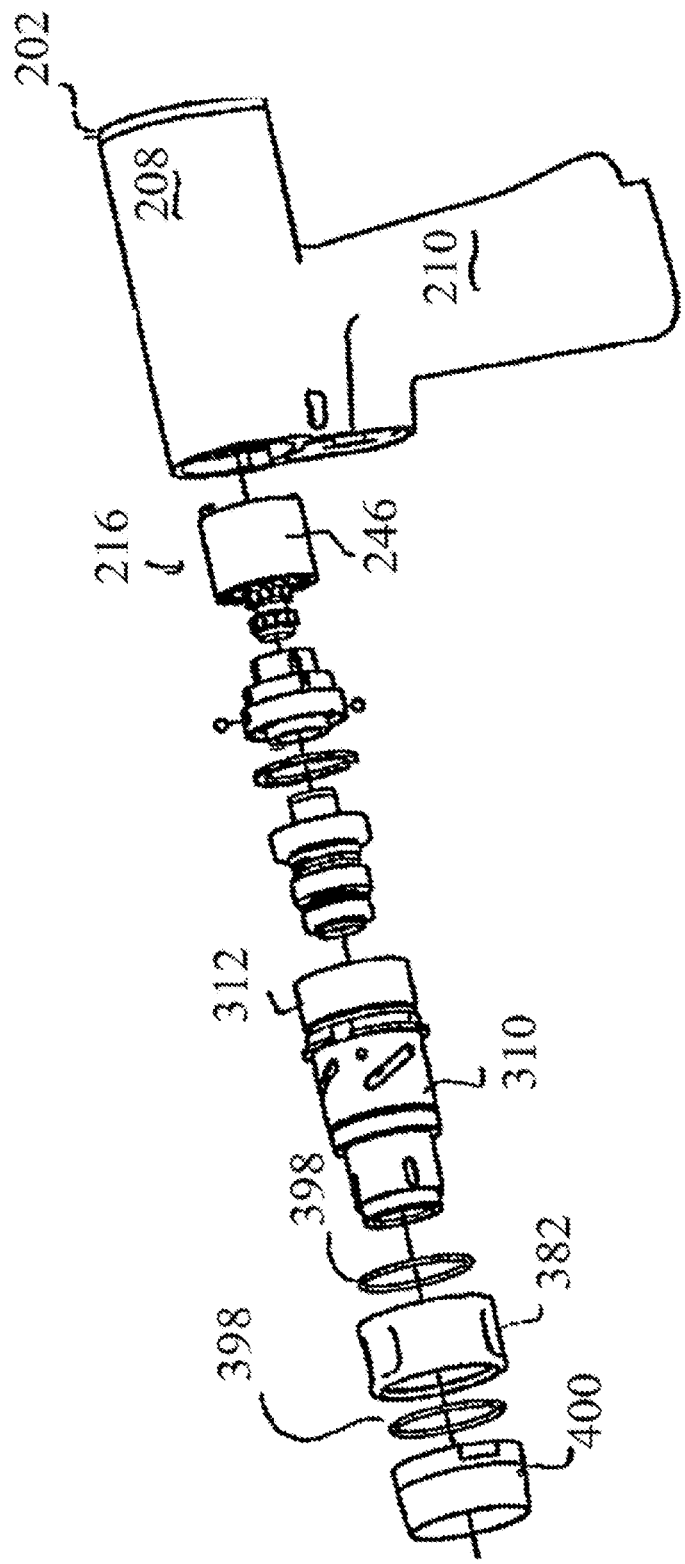
FIG. 7 is a partially exploded view of the distal front end of the handheld surgical instrument.

A transmission 216 is connected to the exposed distally located front end of the motor output region 206. The transmission 216 includes gears that reduce the speed and increase the torque of the rotational moment output by the motor output region 206. The transmission 216 has two rotating drive heads 266, 272 (as shown in FIGS. 7-8). Owing to the arrangement of the gears forming the transmission 216, the rotation of motor output region 206 causes drive heads 266, 272 to simultaneously rotate at different speeds. Transmission 216 thus functions as a speed reduction assembly that outputs rotational force at two separate speeds.

The handheld surgical instrument 200 further comprises a clutch 224 defining a clutch input region that is operably coupled to the transmission output region such that drive of the transmission output region is configured to cause drive of the clutch input region. The clutch in the first position may be configured to interface the clutch input region with one of the two gear sets at a first transmission-clutch interface having a first transmission-clutch backlash such that drive of the transmission output region within the first transmission-clutch backlash does not cause drive of the clutch input region. The clutch in the second position may be configured to interface the clutch input region with the other one of the two gear sets at a second transmission-clutch interface having a second transmission-clutch backlash such that drive of the transmission output region within the second transmission-clutch backlash does not cause drive of the clutch input region.

Figure 6A:
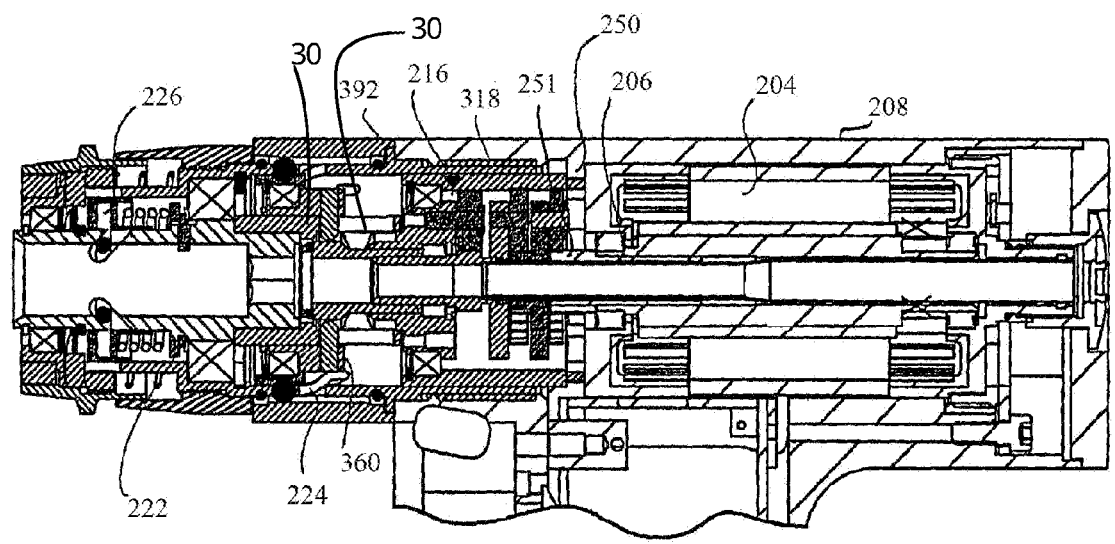
FIG. 6A is a cross sectional view of the front end of the handheld surgical instrument of FIG. 5A along the longitudinal axis.
Figure 6B:
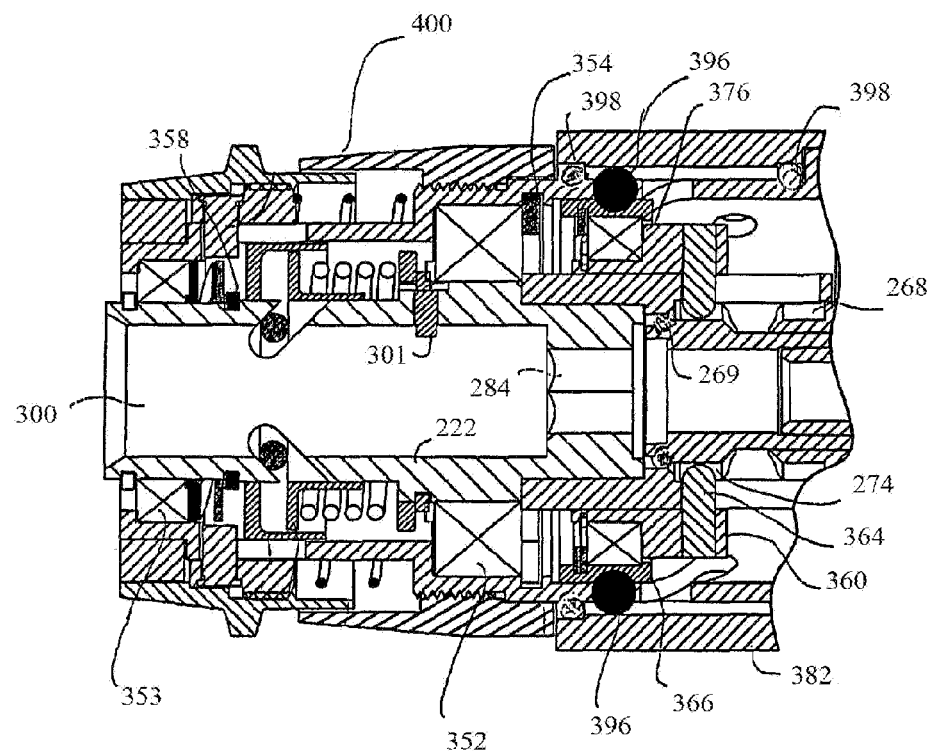
FIG. 6B is an enlarged cross sectional view of the distal end of the handheld surgical instrument of FIG. 6A.

In an exemplary embodiment, the clutch input region may be implemented in the form of pins (as shown in FIG. 6B, 364) that are operably coupled to the transmission output region, which may be implemented in the form of gear sets or drive heads (as shown in FIG. 8, 266, 272), such that the drive of the drive heads is configured to cause drive of the pins 364. The pins 364 are movable to a first position where one of the two gear sets 266, 272 is operably coupled to the pins 364 and configured to cause drive of the pins 364. The pins 364 are further movable to a second position where the other one of the two gear sets 266, 272 is operably coupled to the pins 364 and configured to cause drive of the pins 364. The clutch 224 further defines a clutch output region operably coupled to the output member.

The transmission output region and the clutch input region interface one another in at least one transmission-clutch interface having a transmission-clutch backlash such that drive of the transmission output region within at least one transmission-clutch backlash does not cause drive of clutch input region. Continuing the previous embodiment, when the clutch input region (as shown in FIG. 6B, 364) is in position to engage either one of the two drive heads 266, 272 of the transmission output region, there will be a backlash between pin 364 and drive head 266 or drive head 272 at the backlash interface 1004 (as shown in FIG. 5B).

Figure 12:
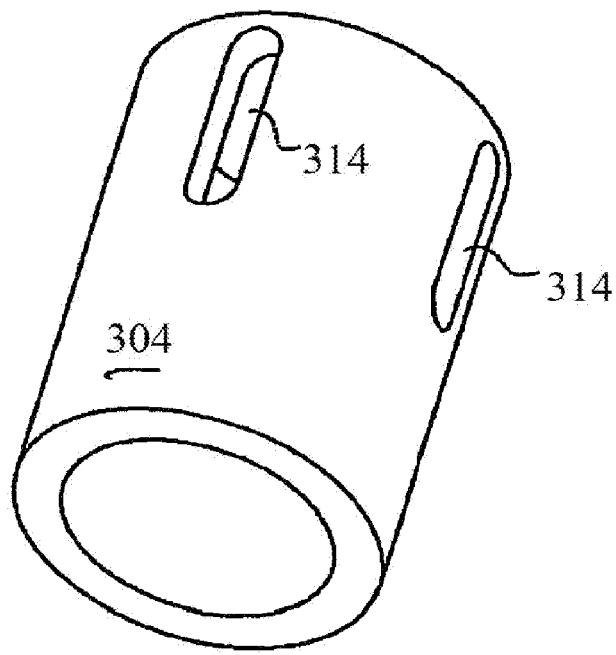
FIG. 12 is a perspective view of a clutch output region of a clutch.

The clutch output region may be statically fixed to the output member, when driven drives the output member through a spindle 222 (as shown in FIG. 6A). Backlash can occur at the interface between the pins of the clutch input region and the drive heads of the transmission output region. Backlash can occur anywhere internal to the clutch, for instance the pins (as shown in FIG. 6B, 222) and the clutch output region (as shown in FIG. 12, 304).

Referring to FIGS. 5B, 6A and 6B, the spindle 222 is rotatably mounted to the housing forward of transmission 216. A clutch 224 selectively connects one of the two transmission drive heads 266, 272 to spindle 222 so that the spindle and connected drive head rotate in unison.

Figure 27:
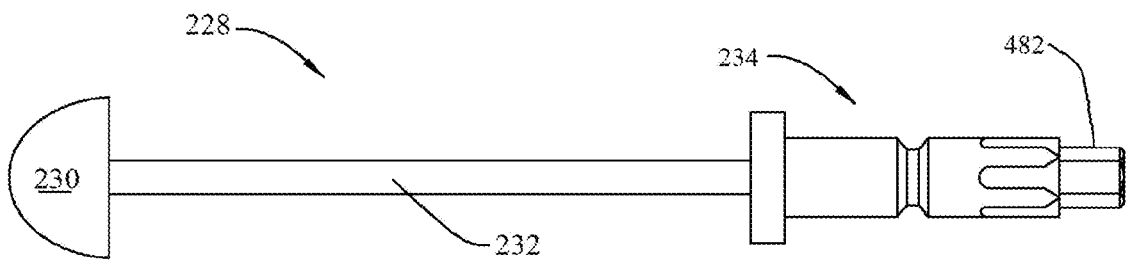
FIG. 27 is a plan view of a surgical end effector.

A mount 226 releasably holds the coupler, which is in the form of a speed-altering surgical attachment 500 (as shown in FIG. 28A) or a surgical end effector 228 (as shown in FIG. 27), to the spindle 222 of the output member. In the embodiment of FIG. 28A, the surgical end effector 228 may be implemented as an acetabular reamer. However, other embodiments of the surgical end effector are contemplated. Surgical end effector 228 has a distal end tissue working head 230, which may be implemented in the form of an acetabular reamer head. Extending proximally from tissue working head 230, surgical end effector 228 has an elongated shaft 232. A mounting head 234 is attached to the proximal end of shaft 232. Coupling head 234 is formed with geometric features that facilitate the rotational coupling of surgical end effector 228 to spindle 222 and minimize wobble of the end effector relative to the handheld surgical instrument 200.

Figure 11:
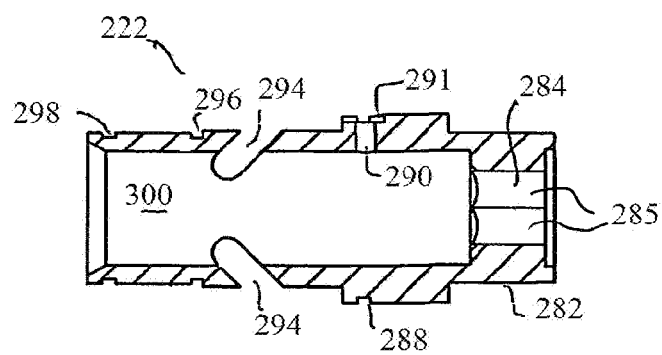
FIG. 11 is a cross sectional view of the spindle for the output member of FIG. 10 taken along line 11-11.

Handheld surgical instrument 200 is constructed so that the distal end of spindle 222 is formed with a bore 300 (as shown in FIG. 11) for receiving the attachment/end effector coupling head 234 (as shown in FIG. 7). Coupler 226 locks the end effector coupling head 234 in spindle bore 300. As a consequence of this engagement, the coupling head 234, and therefore the whole of surgical end effector 228, rotates in unison with the spindle 222.

Transmission 216, now described by reference to FIGS. 6A, 8 and 9, includes a first set of three planet gears 242 (two shown). Planet gears 242 are each rotatably mounted to a generally disc-shaped planet carrier 244. Planet gears 242 and planet carrier 244, as with the remaining planet gears and planet carriers of transmission 216, are housed in a generally tubular-shaped ring gear 246. Ring gear 246 has a smooth outer wall and a toothed inner wall (teeth not illustrated). The teeth of planet gears 242, as well as the teeth of the remaining planet gears 254, 262, engage the teeth of ring gear 146.

Ring gear 246 is statically mounted in the handheld surgical instrument housing head 208 forward of motor 204. To facilitate the static mounting of ring gear 246, the ring gear is formed with two proximally extending feet 248. The feet seat in openings formed in an internal structural web 250 of the housing to block rotation of the ring gear (openings not identified).

Planet gears 242 seat over and engage a pinion gear 251 disposed over motor output region 206 (identified in FIG. 6A). Thus, the rotation of motor output region 206 causes the rotation of planet gears 242 and planet carrier 244.

A first sun gear 252 is integrally mounted to planet carrier 244. In this embodiment, first sun gear 252 is positioned concentric with planet carrier 244 and extends distally forward from planet carrier 244. Sun gear 252 engages a second set of three planet gears 254 (two shown). Planet gears 254 are rotatably disposed around a second planet carrier 256. A tubular post 258 is integrally attached, concentric with and extends distally forward from second planet carrier 256. A set of teeth disposed around the proximal end base of post 258 form a second sun gear 260.

Second sun gear 260 engages a third set of planet gears, four planet gears 262 (one shown). Planet gears 262 are rotatably attached to and disposed around a third planet carrier 264. A first drive head 266 is formed integrally with and extends axially forward from the third planet carrier. The first drive head 266 has a generally circular outer profile. The outer surface of drive head 266 is further shaped to have a plurality of longitudinally extending inwardly concaved, notches 268. The notches 268, which are circumferentially spaced apart, are located around the whole of the circumference of drive head 266. Planet carrier 264 is further formed to have an axially extending through bore 270. Bore 270 extends completely through both the planet carrier 264 and drive head 266.

A second drive head 272 is positioned distally forward of, and concentric with, drive head 266. Drive head 272 has the same outer diameter as drive head 266. Drive head 272 defines notches 274 that have the same profile of notches 268 of the first drive head 266. A tubular-shaped stem 276 extends proximally rearward from drive head 272. In many embodiments of the invention, second drive head 272 and stem 276 are integrally formed. When transmission 216 is assembled, post 258 of the second planet carrier 256 is disposed in bore 270 of third planet carrier 264 and drive head 266. Stem 276 similarly is disposed in bore 270. More particularly, stem 276 is dimensioned to be tightly press fit over post 258. Thus, drive head 272 rotates in unison with the second planet carrier 256. Collectively, post 278 and stem 276 are shaped so that there is a longitudinal separation between drive heads 266, 272.

Drive head 266 and stem 276 are further collectively shaped so that the outer surface of the stem is spaced inwardly of the adjacent bore 270 defining the inner wall of the drive head. This arrangement allows stem 276 to rotate freely relative to the drive head 268. Adjacent the proximal end of stem 276, a bearing assembly 277 extends between post 258 and an adjacent inner circular wall internal to planet carrier 264. More particularly, the planet carrier internal wall against which the outer race of bearing assembly 277 seats defines an elongated groove 279 that is concentric with and has a larger outer diameter than planet carrier bore 270. A retaining ring 280 disposed proximal to the bearing assembly 277 holds the bearing assembly in position. Retaining ring 280 is snap fitted in a groove 281 also formed in the interior of planet carrier 264. The planet carrier 264 is formed so that groove 281 is between the proximal end opening of bore 270 and groove 279 and is of greater diameter than groove 279.

Drive head 272 has a nose 271. Nose 271 extends forward of the portion of the drive head formed with notches 274. An O-ring 269 is disposed over nose 271. O-ring 269 is fitted over the drive head nose 271 portion immediately distal to the portion of the nose that defines notches 274.

A bearing assembly 275 rotatably holds planet carrier 264 to the static ring gear 246. Bearing assembly 275 has an outer race (not illustrated) seated in the perimeter of a counterbore 247 that forms the open end of ring gear 246. The inner race of bearing assembly 275 (not illustrated) seats against an annular step 278 formed in the outer perimeter of the third planet carrier 264. A retaining ring 267 holds bearing assembly 275 and, by extension, the moving components of gear train 216 in ring gear 246. Retaining ring 267 is snap fitted in a groove 273 formed in the inner wall of the ring gear 246 that defines counterbore 247.

As shown in FIG. 5B, the motor output region may be implemented as the pinion gear 251, which interfaces with the transmission input region, which may be implemented as the first set of planet gears, 242, at the motor-transmission interface having a first backlash interface 1000. Also in this embodiment, the transmission may have a backlash interface 1002 between the first sun gear 252 and the second planet gears 254 and a backlash interface 1008 between the second sun gear 260 and the third set of planet gears 264.

Figure 10:
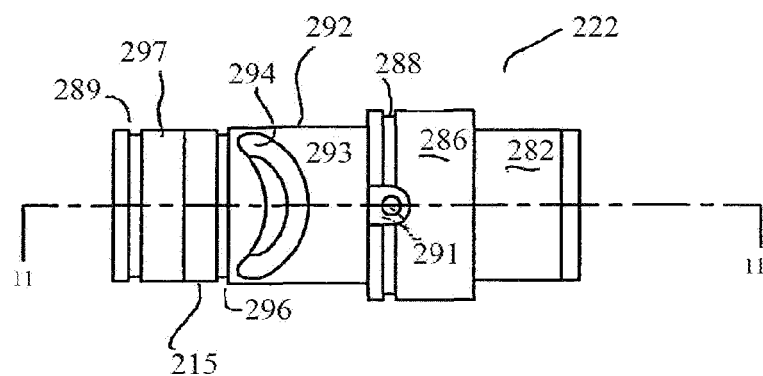
FIG. 10 is a plan view of the spindle of the handheld surgical instrument.

Referring to FIGS. 10 and 11, the spindle 222 may be implemented in the form of a single piece of metal that has circular sections of different diameters. At the most proximal end, spindle 222 comprises the coupler in the form of a head 282 defining a bore 284 with a hexagonal cross-sectional profile. However, it is contemplated that the bore can have a cross-section profile in the form of any suitable shape. Bore 284 is configured to closely slip fit receive the proximal end of the surgical end effector coupling head 234 fitted to the surgical end effector 228. The close fitting is required because the inner surfaces 285 of the head 282 that define bore 284 are the surfaces that transmit the torque to the surgical end effector 228.

Extending distally from head 282, spindle 222 has a collar 286. Collar 286 is shaped to have an outer diameter greater than that of head 282. Immediately proximal of the distal end of the collar 286, the collar is shaped to have a groove 288 that extends circumferentially around the outer surface of the collar. Collar 286 is further formed to define an opening 290 that extends laterally through the collar. Opening 290 is located to extend through an arcuate section of the collar 286 that defines the base of groove 288. Opening 290 extends from a base of a recess 291 cut into the outer surface of collar 286.

Spindle 222 further comprises the output member formed as a stem 292 that projects distally from collar 286. Stem 292 has a number of sections with different outer diameters. A proximal section 293 adjacent collar 286 has a diameter approximately equal to that of sleeve head 282. Stem section 293 is formed to have two diametrically opposed receiving slots 294. Each receiving slot 294 is in a plane that, relative to the longitudinal axis of spindle 222, extends diagonally forward. In some embodiments of the invention, each slot 294 is in a plane that, relative to the longitudinal axis of the spindle 222, is at an angle of approximately 450. Thus, as seen in FIG. 10, when viewing a slot 294 from the front, a slot 294 appears to have a curved profile.

Distally from section 293, the stem 292 is further formed to have a circumferential groove 296. Forward of groove 296 stem 292 has an intermediate section 295. Section 295 has a diameter slightly less than that of proximal section 293. The reduced diameter of stem section 295 allows below discussed wave spring 357 (as shown in FIG. 26) to freely flex.

Forward of section 295, spindle stem 292 is formed with a distal end section 297. Stem section 297 has an outer diameter between the diameters of sections 293 and 295. The inner race of a bearing assembly 353 (as shown in FIG. 6A) tightly fits over stem section 297. A groove 298 extends circumferentially around the outer surface of stem 292. Groove 298 is located immediately proximal to the distal end of stem section 297, which is also the distal end of spindle 222.

Spindle 222 is further formed to have a bore 300 that extends from the distal end, through stem 292 and collar 286 to bore 284. Bore 300 is concentric and contiguous with bore 284. In preferred embodiments, bore 300 has a circular cross sectional profile, though that need not always be the case. Bore 300 is dimensioned to facilitate the close slip fitting of a coupling head 234 of the surgical end effector 228 as discussed below.

Figure 26:
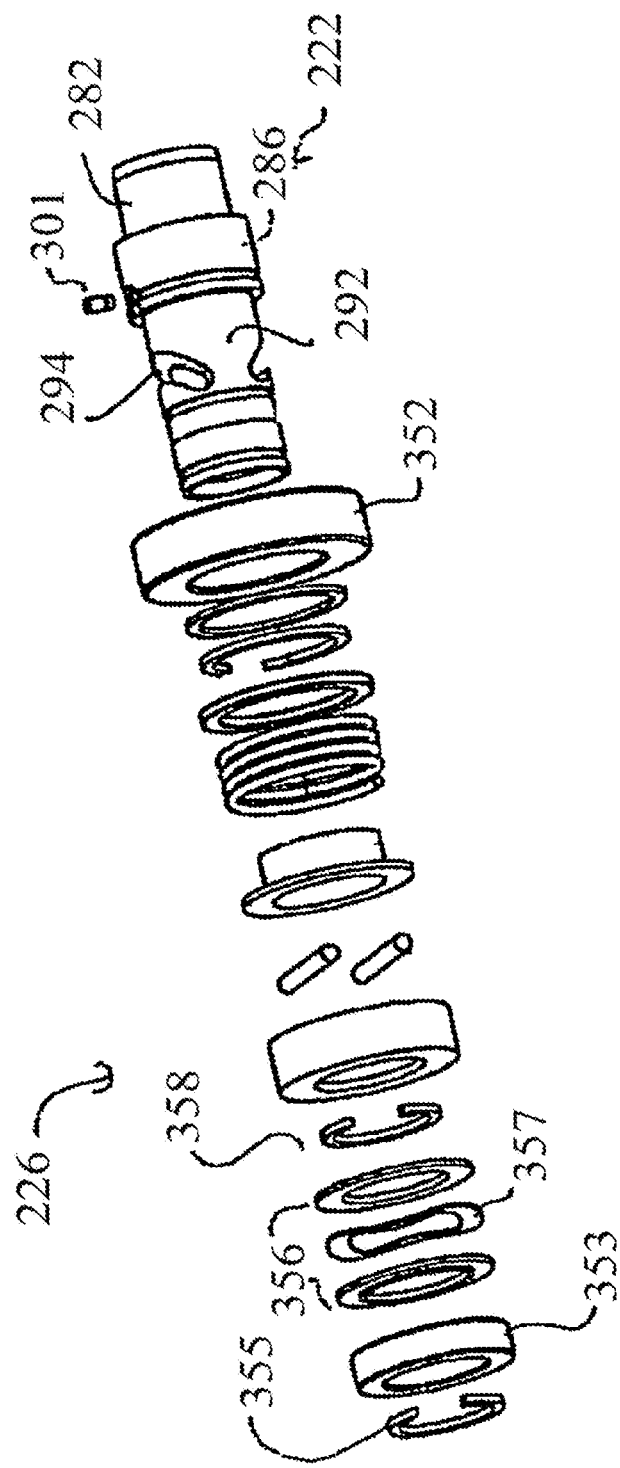
FIG. 26 is an exploded view of the coupler.

A pin 301 (as shown in FIG. 26) is fitted in spindle opening 290 (as shown in FIG. 11), so as to be directed to the longitudinal center axis of the spindle 222. Pin 301 extends into bore 300.

Figure 13:
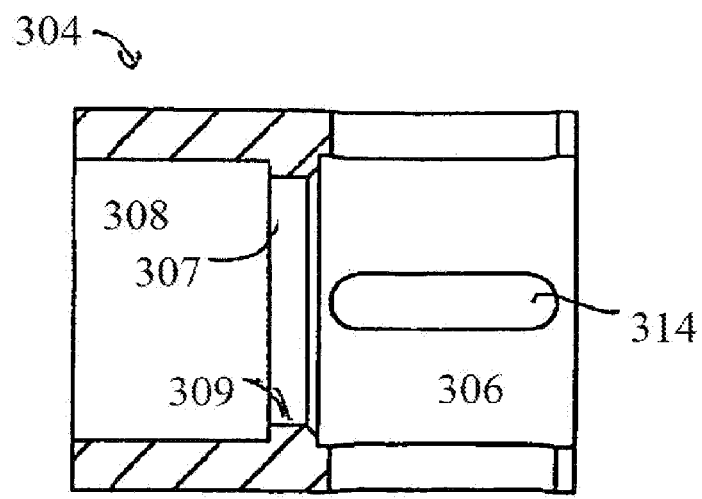
FIG. 13 is a cross sectional view of the clutch output region.

Referring to FIGS. 12 and 13, a generally tubular-shaped clutch output region 304 is tightly fitted to the spindle 222. Clutch output region 304 may have a constant outer diameter. The clutch output region 304 is further formed to have a proximal end bore 306 that extends distally forward from the proximal end of the coupler. In this exemplary embodiment, proximal end bore 306 extends approximately half way through the length of the coupler. Clutch output region 304 also has a distal end bore 308 that extends rearward from the distal end of the clutch output region. Distal end bore 308 has a diameter that facilitates the compression fitting of sleeve head 282 in the bore 308.

Between the proximal end bore 306 and distal end bore 308, clutch output region 304 is formed to have a circular void space 307. The outer perimeter of void space 307 is defined by a circular flange 309 that extends inwardly from the inner walls of clutch output region 304 that define bores 306 and 308 and space 307. Flange 309 has a distally-directed, laterally-extended annular face against which the proximally-directed face of sleeve head 282 abuts. Clutch output region 304 is further formed to have four longitudinally extending slots 314. Each slot 314 extends from the outer surface of the clutch output region 304 into the proximal end bore 306. Slots 314 are uniformly spaced apart from each other around the perimeter of the clutch output region 304.

Clutch output region 304 itself is shaped to have an outer diameter that is slightly greater than the outer diameter of spindle collar 286. When the spindle head 282 is inserted in the clutch output region 304, the distal end face of the clutch output region forms an annular step around the proximal end of the spindle collar 286.

Referring back to FIG. 6A, it can be seen that when surgical handheld instrument 200 is assembled, the spindle 222 and clutch output region 304 sub-assembly are fitted in the housing 208 so that gear train drive heads 266, 272 of the transmission output region are disposed in the proximal end bore 306 of the clutch output region. Clutch output region 304 is shaped so that the inner wall that defines the proximal end bore 306 is spaced away from the drive heads 266, 272. Drive head nose 271 seats in clutch output region void space 307. O-ring 269 abuts the adjacent inner face of clutch output region flange 309.

Figure 15:
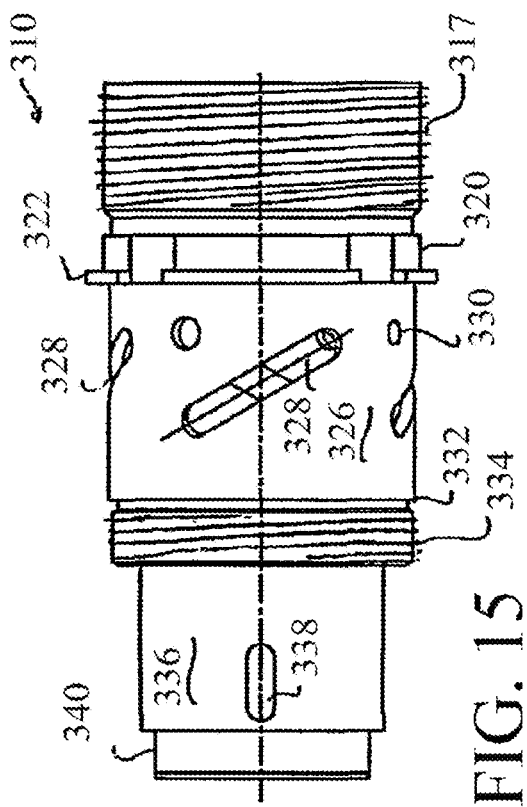
FIG. 15 is a plan view of the rotary housing of the output member.
Figure 16:
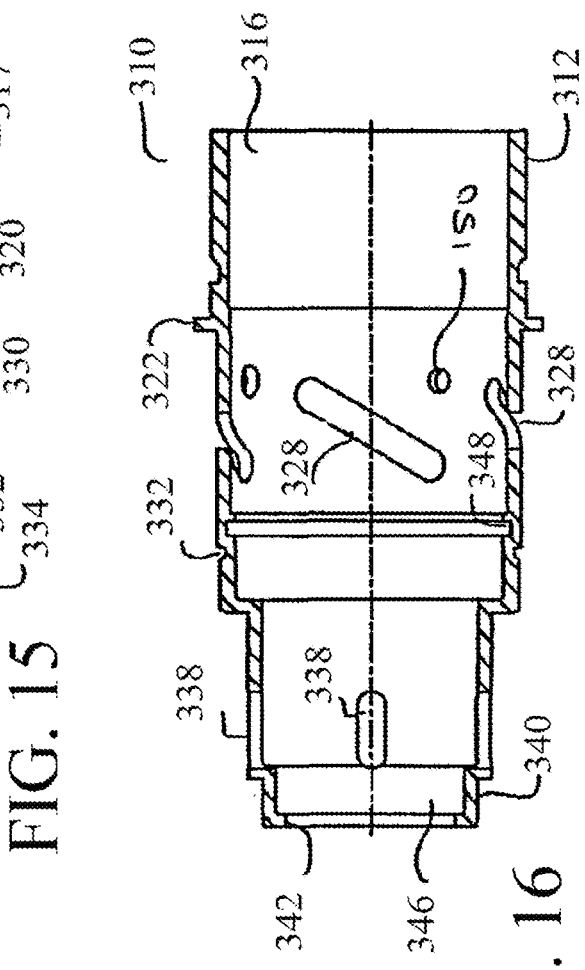
FIG. 16 is a cross section view of the rotary housing of the output member of FIG. 15 taken along line 16-16.
Figure 14:
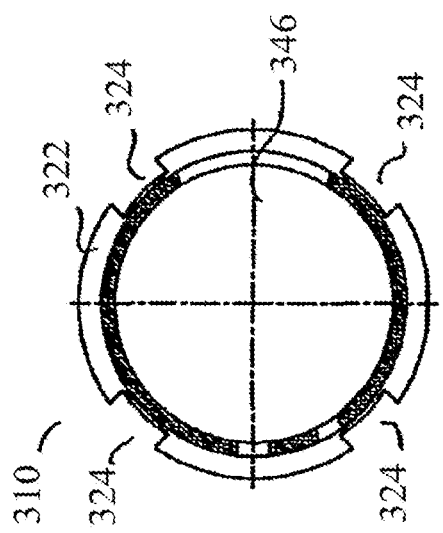
FIG. 14 is an end view of a rotary housing for the output member of the handheld surgical instrument.
Figure 17:
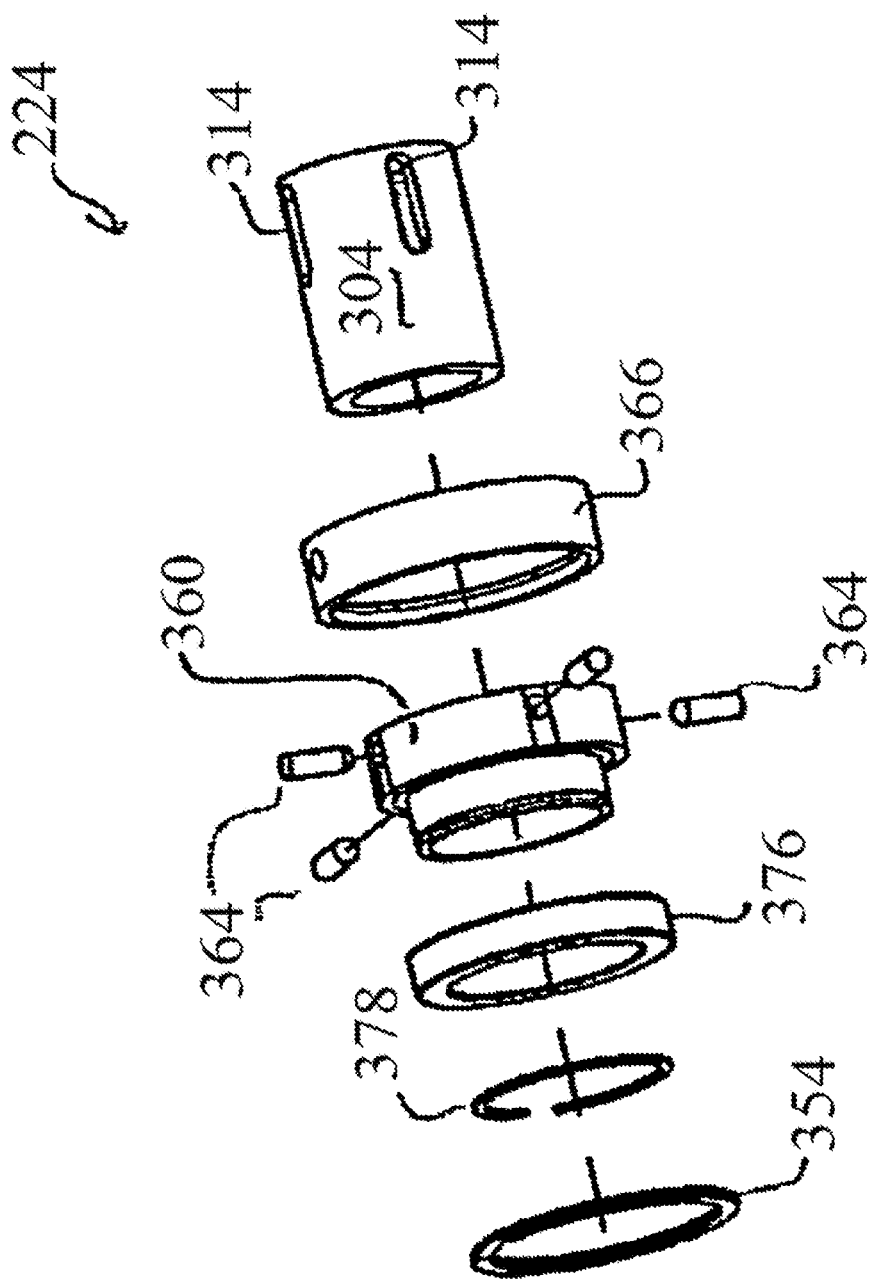
FIG. 17 is an exploded view of the clutch.
Figure 18:
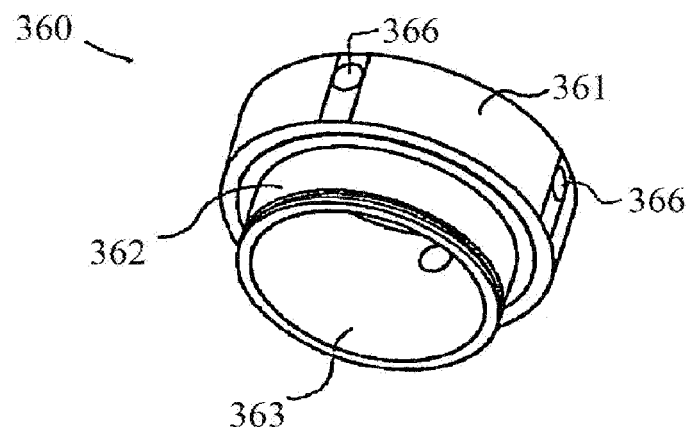
FIG. 18 is a perspective view of the inner shifter of the clutch.
Figure 19:
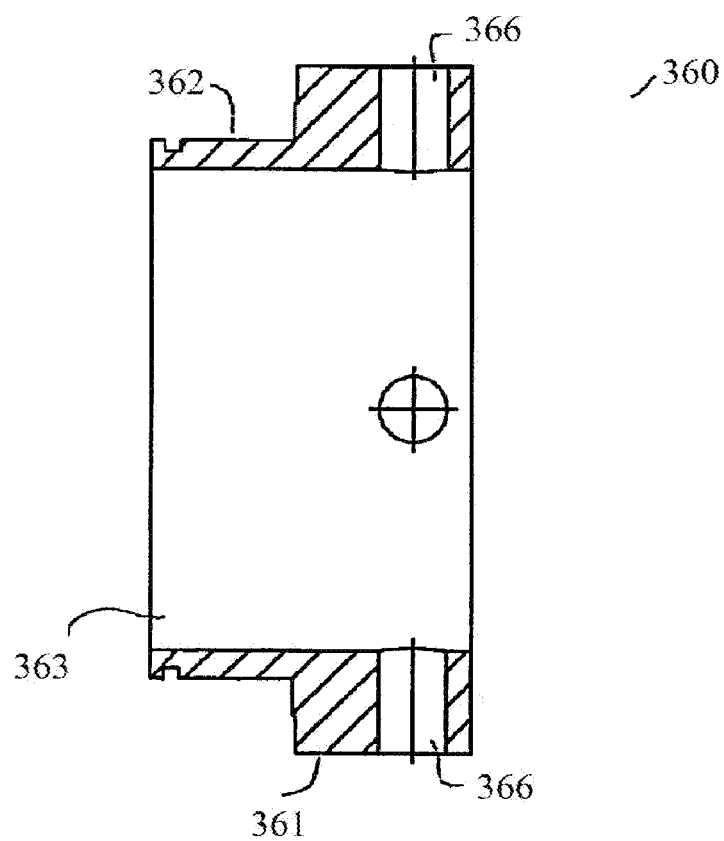
FIG. 19 is a cross sectional view of the inner shifter of the clutch.

Transmission 216, clutch output region 304, and spindle 222 are substantially disposed in a rotary housing 310 that extends distally forward from the front of handheld surgical instrument housing 202. The rotary housing 310, now described by reference to FIGS. 14-16, is formed from a single piece of metal that has a number of circular cross-sectional sections. The most proximal section of the rotary housing 310 is a base 312. The outer surface of rotary section base 312 adjacent the proximal end of the rotary section is formed with threading 317 (seen in FIG. 15 only). Base 312 is formed with an open ended bore 316. Bore 316 is dimensioned to facilitate the loose slip fitting of the base over transmission ring gear 246. When handheld surgical instrument 200 is assembled, base threading 317 engages complementary threading 318 formed around an inner wall of housing 208 (as shown in FIG. 6A). This threaded engagement holds rotary housing 310 to the handheld surgical instrument housing 208.

Extending distally of the threaded section, rotary housing base 312 is formed with a section 320 with a smooth outer wall. Forward of base section 320, the rotary housing 310 has a flange 322 that extends radially outward of base 312. Flange 322 is the structural component of the rotary housing 310 that stops proximal movement of the rotary housing when the housing is screw fitted to the handheld surgical instrument housing 208. Rotary housing 310 is further formed to define four slots 324 that extend through base section 320 and flange 322. Slots 324 are uniformly spaced apart from one another about the circumference. The slots 324 function as spaces for receiving a fastening tool (not illustrated) used to screw secure the rotary housing 310 to the handheld surgical instrument housing 208 during manufacture.

Forward of flange 322, rotary housing 310 forms a clutch sleeve 326. Clutch sleeve 326 has a diameter slightly less than that of base 312. The clutch sleeve 326 is formed to have four slots 328 uniformly spaced apart from one another about the circumference. Slots 328 extend diagonally downwardly around the outer circumference of the clutch sleeve 326. Four holes 330 are uniformly spaced apart from one another about the circumference of the clutch sleeve 326. Holes 330 are in a common circumferential section of the clutch sleeve located proximal to the proximal ends of slots 328. Holes 330 are provided to facilitate manufacture and disassembly of the handheld surgical instrument 200.

A groove 332 is formed in the clutch sleeve 326 to extend circumferentially around the outer surface of the sleeve. Groove 332 is located proximally rearward of the forward distal end of the clutch sleeve 326. The outer surface of the clutch sleeve 326 located distal to groove 332 and extending to the distal end of the clutch sleeve is provided with threading 334 (seen in FIG. 15).

Projecting distally forward of clutch sleeve 326, rotary housing 310 has a coupling neck 336. Coupling neck 336 has a diameter less than that of clutch sleeve 326. The coupling neck 336 is formed to define four slots 338 uniformly spaced apart from one another. Slots 338 extend longitudinally along the coupling neck 336 and are generally located in the most distal portion of the coupling neck 338.

A head 340 forms the most distal section of rotary housing 310. Head 340 extends forward from and has a diameter less than that of coupling neck 336. Head 340 is formed with an inwardly directed circumferential lip 342. Lip 342 defines the open distal end of the rotary housing, (distal end opening not identified).

Rotary housing 310 is further formed so that extending axially and distally forward from bore 316 there is a bore 346 that extends to the distal end of the housing. Bore 346 has sections of different diameters. The diameters of the different bore sections (not identified) are generally sized relative to each other in the same manner as the outer diameters of the clutch sleeve 326 and coupling neck 336, and head 340 correspond to each other. The rotary housing 310 is further formed to have a groove 348 that extends inwardly from a housing inner wall that defines one of the sections of bore 346. Specifically, groove 348 is formed in the housing clutch sleeve 326 so as to be immediately distal to the circular slice of the sleeve 326 in which outer circumference groove 332 is formed.

Bearing assemblies 352, 353, seen best in FIGS. 6B and 26, rotatably hold the spindle and outer coupler sub-assembly to the rotary housing 310. The outer race of bearing assembly 352 (outer race not illustrated) seats against the bore 346 defined by the inner wall of the housing clutch sleeve 326. The proximal end of the bearing race seats against the stepped inner annular surface of the rotary housing between the clutch sleeve 326 and the coupling neck 336. The proximally-directed face of the outer race of bearing assembly 352 abuts a retaining ring 354 disposed in bore 346. Retaining ring 354 is snap fitted in rotary housing groove 348.

The inner race of bearing assembly (not illustrated) is press fit over spindle collar 286. When the handheld surgical instrument 200 is assembled, the proximal end of the inner race of bearing assembly is disposed against the annular portion of the distally directed face of the adjacent clutch output region 304. As discussed above, the outer race of bearing assembly 352 is blocked from distal movement by the adjacent inner walls of the rotary housing 310. Thus, the abutment of the clutch output region 304 against the inner race of bearing assembly 352 by extension blocks distal movement of the spindle and outer coupler sub-assembly.

Bearing assembly 353 extends between the distal front end of spindle stem 292 and the adjacent inner wall of the rotary housing head 340. The outer race of bearing assembly (not illustrated) seats against the inner wall of the rotary housing 310 within the housing head 340. The bearing assembly outer race also abuts the proximally-directed surface of rotary housing lip 342. The distally directed face of the inner race of bearing assembly 353 seats against a retaining ring 355. Retaining ring 355 is snap fitted into groove 298 of spindle stem 292. Thus, collectively, rotary housing lip 342 and retaining ring 355 block forward movement of bearing assembly 353.

Washers 356 and 357 and retaining ring 358 cooperate to prevent proximal movement of bearing assembly 353. Two washers 356 are provided. The more distal of the two washers 356 is disposed against the proximally-directed face of the bearing assembly 353. Washer 357, which is flexible wave washer, is sandwiched between the distal and proximal washers 356. The retaining ring 358 seats in spindle groove 296. The retaining ring 358 extends above the outer surface of the surrounding spindle sleeve 292. When handheld surgical instrument 200 is assembled, the exposed portion of the retaining ring 358 blocks proximal movement of washers 356 and 357 and, therefore, similar movement of bearing assembly 353. Wave washer 357 is provided to ensure that, in the event of manufacturing variations, the distal washer 356 is disposed against the bearing assembly 353.

Washers 356 are L-shaped. The short vertical sections of the washers (not identified) are disposed around the outer surface of the spindle stem 292. The washer 356 closest to bearing assembly 353 is positioned so its vertical section is against the inner race of the bearing assembly. This arrangement holds the washer 356 off the inner race of the bearing assembly 353. The washer 356 adjacent retaining ring 358 is positioned so that its vertical section abuts the retaining ring.

When the spindle and clutch output region sub-assembly is so positioned, transmission output region drive heads 266, 272 are both seated in the clutch output region proximal end bore 306. Slots 314 are formed in the clutch output region 304 so as to extend over the drive heads 266, 272. Also, the components of this embodiment are dimensioned so that when the spindle 222 is seated in the rotary housing 310, the most distal end of the spindle projects a slight distance forward of the surrounding distal end of the rotary housing.

Figure 20:
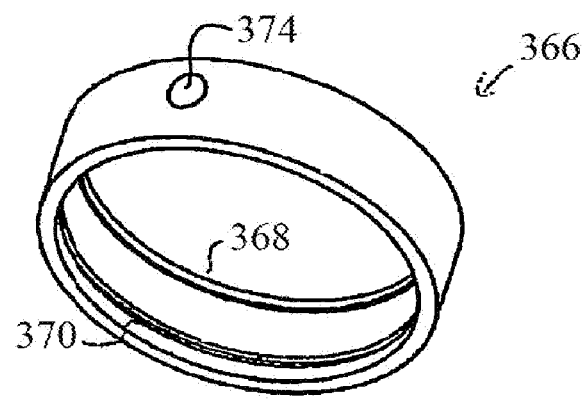
FIG. 20 is a perspective view of the shifter housing of the clutch.
Figure 21:
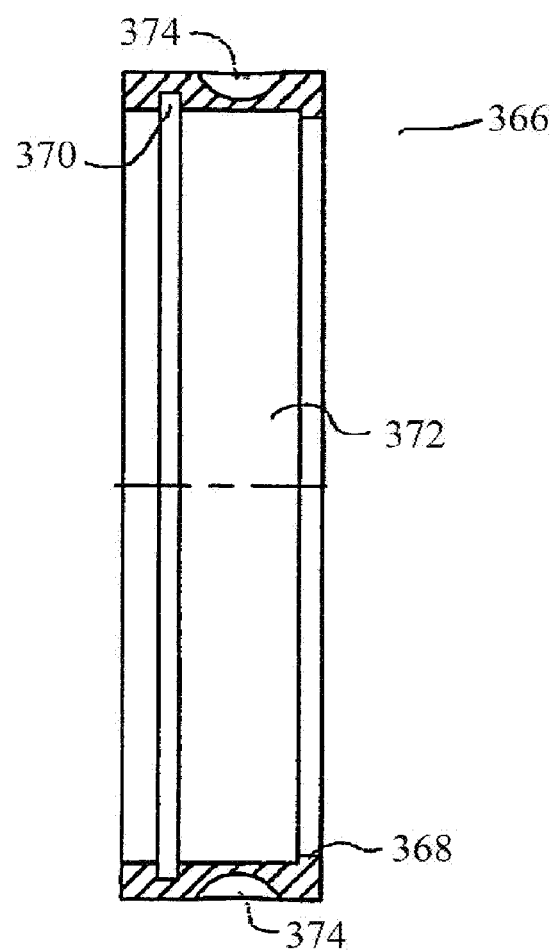
FIG. 21 is a cross sectional view of the shifter housing of the clutch.

Referring now to FIGS. 6A and 21, the clutch 224 includes a circular inner shifter 360 disposed inside the rotary housing clutch sleeve 326 over the clutch output region 304. As best seen in FIGS. 20 and 21, inner shifter has a base 361. Extending distally forward from base 361, the inner shifter 360 is shaped to have a head 362. Head 362 has an outer diameter less than that of base 361. A constant diameter bore 363 extends axially through the inner shifter 360 from the proximal end of base 361 to the distal end of head 362.

Inner shifter 360 is shaped so that when the clutch output region 304 is seated in bore 363, the shifter is able to move longitudinally along the length of the outer coupler. Clutch 224 includes four torque pins 364 uniformly spaced apart from one another about the circumference and extending radially inwardly from the inner shifter base 361. Each torque pin 364 is seated in a laterally extending opening 365 formed in the inner shifter base 361. Each torque pin 364 extends through an associated one of the clutch output region slots 314. Torque pins 364 are of sufficient length so end tips of the pins can seat in notches 268 and 274 of transmission drive heads 266, 272, respectively.

Referring to FIGS. 20 and 21, a shifter housing 366 disposed over the inner shifter 360 longitudinally moves the inner shifter 360 over the clutch output region 304. The shifter housing 366 is generally in the form of a constant outer diameter, ring-shaped structure. Shifter housing 366 is further formed to, at the proximal end, have an inwardly extending lip 368. A groove 370 extends inwardly from the annular inner wall of the shifter housing 366 that defines the center opening 372 through the housing. Groove 370 is located proximal to the distal end face of the shifter housing 366. The shifter housing 366 is further formed to define two diametrically opposed spherical indentations 374 on the outer surface.

Shifter housing 366 is disposed in the rotary housing clutch sleeve 326. Inner shifter head 362 is positioned inside the shifter housing 366. A bearing assembly 376 is disposed between the outer circumferential wall of the inner shifter head 362 and the adjacent inner wall of the shifter housing 366. The proximal end of bearing assembly 376 abuts the adjacent distally-directed annular surface of the inner shifter base 361 that projects radially beyond head 362. The outer perimeter of the distally directed face of bearing assembly 376 abuts a retaining ring 378 fitted to the shifter housing 366. Specifically, retaining ring 378 is snap fitted in shifter housing groove 370. Thus, the capture of the opposed ends of bearing assembly 376 by the inner shifter base 361 and retaining ring 378 lock the inner shifter 360 and shifter housing 366 together for longitudinal movement. Bearing assembly 376 allows the inner shifter 360 and shifter housing 366 to axially rotate relative to each other.

Figure 22:
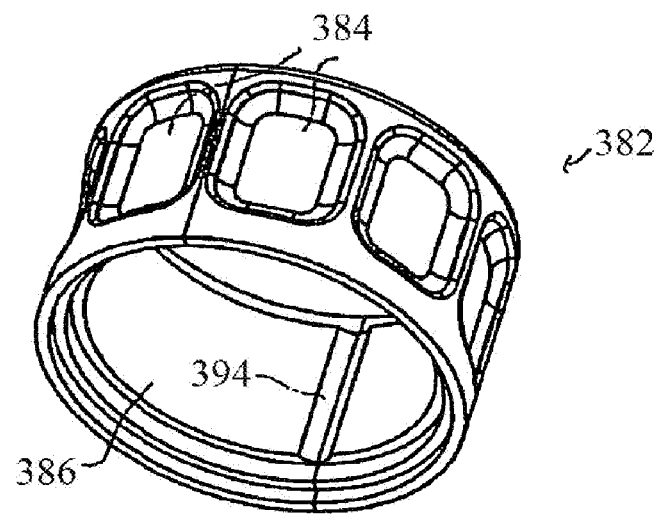
FIG. 22 is a perspective view of the shift ring of the clutch.
Figure 23:
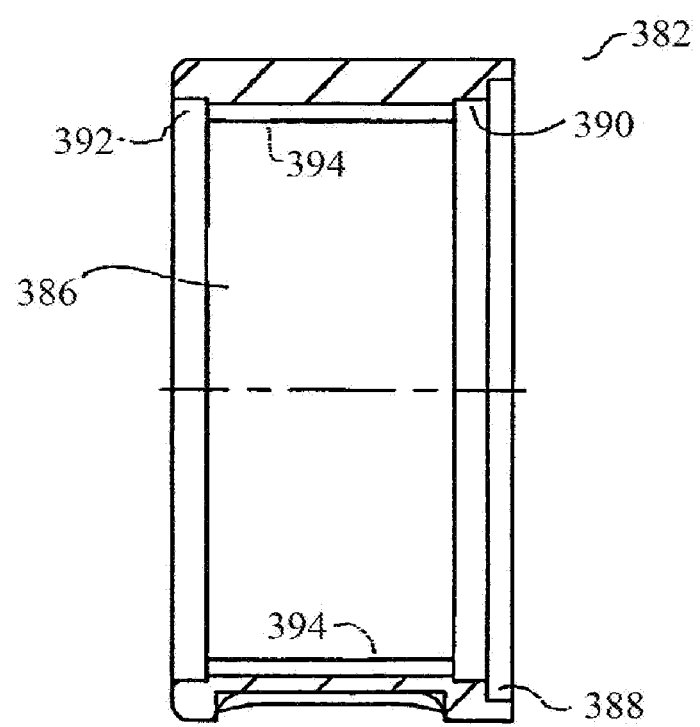
FIG. 23 is a cross sectional view of the shift ring of the clutch.

Referring to FIGS. 22 and 23, a shift ring 382 rotatably mounted over the rotary housing clutch sleeve 326 is manually actuated to set the longitudinal position of the shifter housing 366 and, by extension, the inner shifter 360. The shift ring 382 is generally in the form of a tubular member. Indentations 384 formed in the outer surface of the shift ring 382 facilitate the finger grasping of the ring. The shift ring 382 is further shaped to define an axially extending through bore 386. Bore 386 is dimensioned to allow the shift ring 382 to rotate over the underlying rotary housing clutch sleeve 326. At the proximal end, shifter ring defines a first counterbore 388 that forms the proximal end opening into bore 386. A second counterbore 390 is located between the first counter bore 388 and bore 386. The second counterbore 390 has a diameter between that of bore 386 and counterbore 388.

At the distal end, shift ring 382 is formed to have a third counterbore 392. The third counterbore 392 forms the distal end opening into bore 386. The second and third counterbores 390 and 392, respectively, are of identical diameter. The inner wall of shift ring 382 that defines bore 386 is further formed to define two longitudinally extending, diametrically opposed concave grooves 394. Each groove 394 extends from the second counterbore 390 to the third counterbore 392.

When handheld surgical instrument 200 is assembled, ball bearings 396 transfer the rotational motion of shift ring 382 into axial motion that displaces the shifter housing 366. Each ball bearing 396 is seated in opposed ones of the rotary housing clutch sleeve slots 328. Two ball bearings 396 are provided; there are four slots 328. The additional slots 328 aid component orientation during assembly of the handheld surgical instrument 200. Inside the rotary sleeve 310, each ball bearing 396 seats in a separate one of the indentations 374 formed in the shifter housing 366. Outside of rotary housing 310, each ball bearing 396 seats in a separate one of the grooves 394 formed in clutch input region 382.

When handheld surgical instrument 200 is assembled, rotary housing flange 322 seats in the clutch input region first counterbore 388. O-rings 398 extend between the outer circumferential face of rotary housing 310 and the inner walls of clutch input region 382. A first O-ring 398 is seated in the annular space of clutch input region second counterbore 390. The second O-ring 398 is seated is seated in the clutch input region third counterbore 392. Both O-rings 398 extend over the smooth outer surface of the rotary housing clutch sleeve 326.

Figure 24:
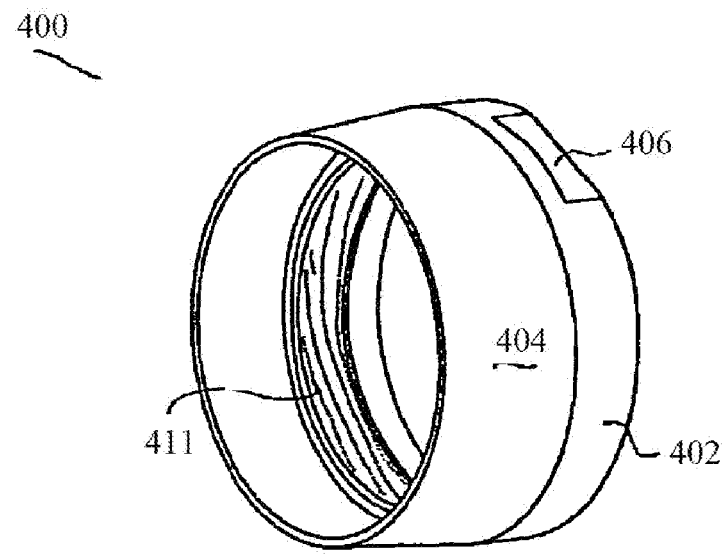
FIG. 24 is a perspective view of the shift ring nut of the clutch.
Figure 25:
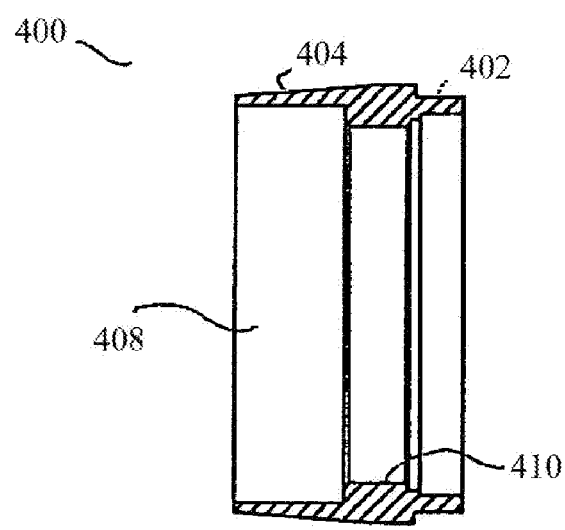
FIG. 25 is a cross sectional view of the shift ring nut of the clutch.

Referring to FIGS. 24 and 25, a shift ring nut 400 holds the shift ring 382 to the rest of the handheld surgical instrument 200. Shift ring nut 400 is generally tubular-shaped. The shift ring 400 is formed to have a base 402 with a generally constant outer diameter. Forward of base 402, shift ring nut 400 has a head 404. Extending distally forward, the outer diameter of the shift ring head 404 tapers inwardly. The shift ring nut 400 is further formed to define two opposed flats 406 in the proximal end of the outer surface of base 402. Flats 406 receive a fastening tool used to screw secure the shift nut 400 to the rotary housing 310 during assembly.

Bore 408 extends axially through the shift ring nut 400 from the proximal end to the distal end. The shift ring nut 400 is further formed to have an inwardly stepped annular lip 410 that extends inwardly from the inner circular wall that defines bore 408. The inner round face of lip 410 is formed with threading 411 (as shown in FIG. 24). The shift ring nut 400 is screw secured to the rotary housing by engaging shift ring nut threading 411 with threading 334 on the rotary housing clutch sleeve 326.

Clutch 224 is then set to couple the spindle 222 to one of the gear train drive heads 266, 272 so that the spindle rotates with the selected drive head. Specifically, the clutch 224 is set so that torque pins 364 of the clutch input region seat in the notches 268, 274 of the drive head 266, 272 of the transmission output region, respectively, with which the spindle is to be connected. The setting of the torque pins 364, e.g., the longitudinal positioning of the torque pins 364, is performed by rotating clutch shift ring 382. The rotation of shift ring 382 results in the helical movement of ball bearings 396 in rotary housing slots 328. The longitudinal displacement of ball bearings 396 results in an identical longitudinal displacement of the shifter housing 366. The longitudinal movement of the shifter housing 366 causes a like movement of the inner shifter 360.

Since torque pins 364 are integral with inner shifter 360, longitudinal displacement of the inner shifter results in the selective seating of the pins in either the notches 268 of the proximally located drive head 266 or notches 274 of the distally located drive head 272.

Handheld surgical instrument 200 is now ready for operating. The depression of trigger switch 212 results in the actuation of motor 204. Motor output region 206 rotates. Transmission 216 reduces the rotation moment output by shaft to two different speeds. Specifically, the gears internal to the gear train cause drive head 266 to rotate at a first reduced speed. Drive head 272 is caused to rotate at a second reduced speed less than the first reduced speed.

Depending on the setting of the clutch 224, the torque pins 364 are seated in the notches 268, 274 of one of the drive heads 266, 272, respectively. The torque pins 364 thus rotate at the speed of the drive head 266, 272 with which the pins are engaged. The torque pins 364 extend through the clutch output region slots 314. Consequently, the rotation of the torque pins results in a like movement of the clutch output region 304 and, therefore, the output member via spindle 222. Since the coupling head boss 482 is relatively closely fitted in the spindle bore 284, and these components have non-circular cross sectional profiles, rotary motion of the spindle 222 is transferred by boss 482 to the coupling head 234 and the rest of the surgical end effector 228.

Figure 28B:
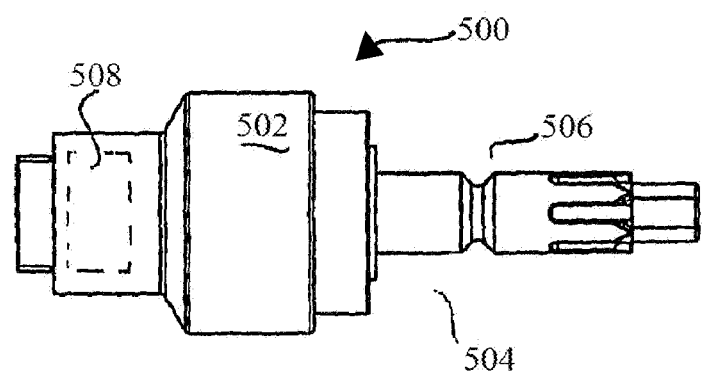
FIG. 28B is an exploded view of the handheld surgical instrument and the speed-altering surgical attachment having multiple interfaces with backlash.
Figure 28A:
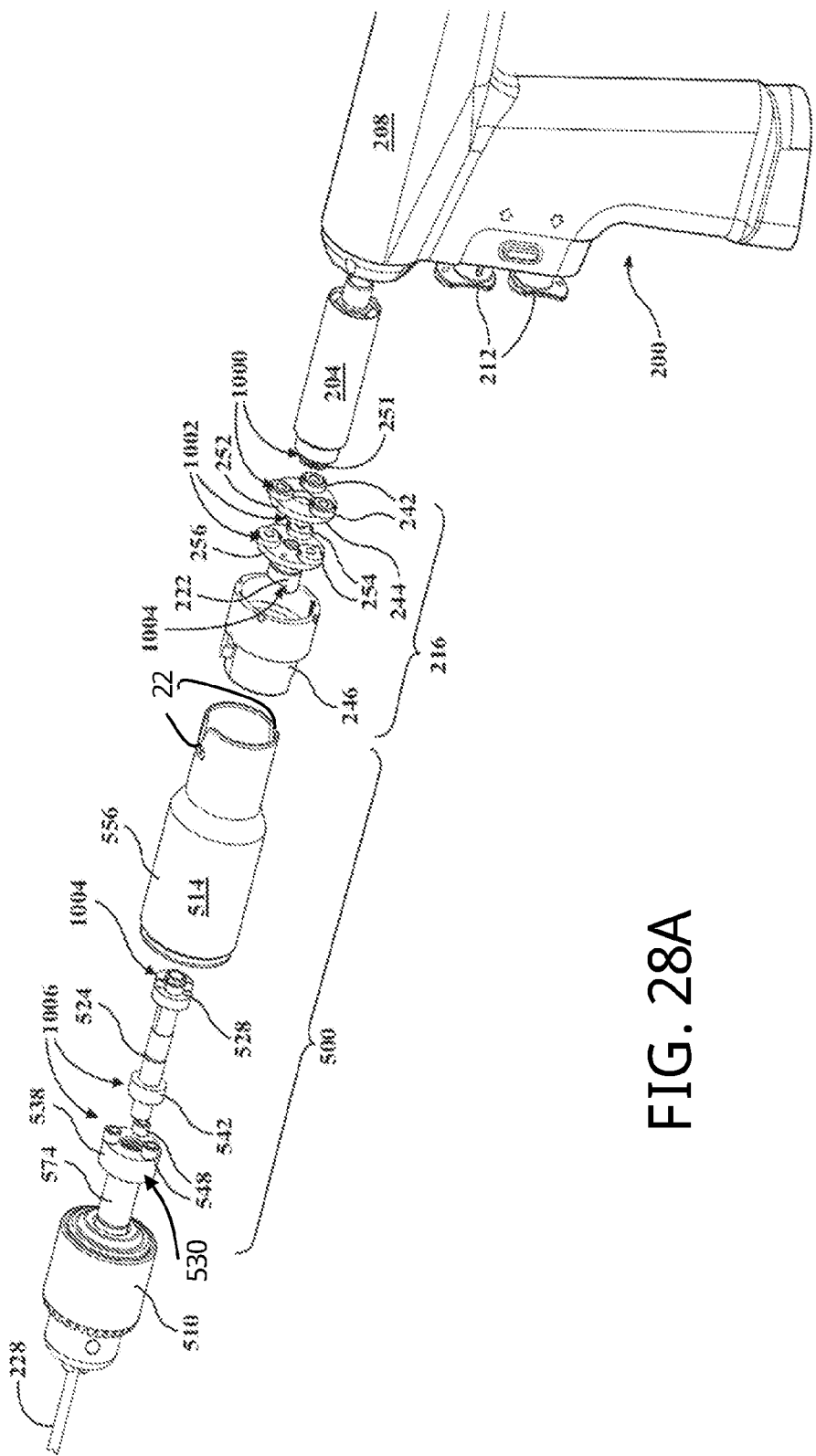
FIG. 28A is a plan view of an speed-altering surgical attachment.
Figure 29:
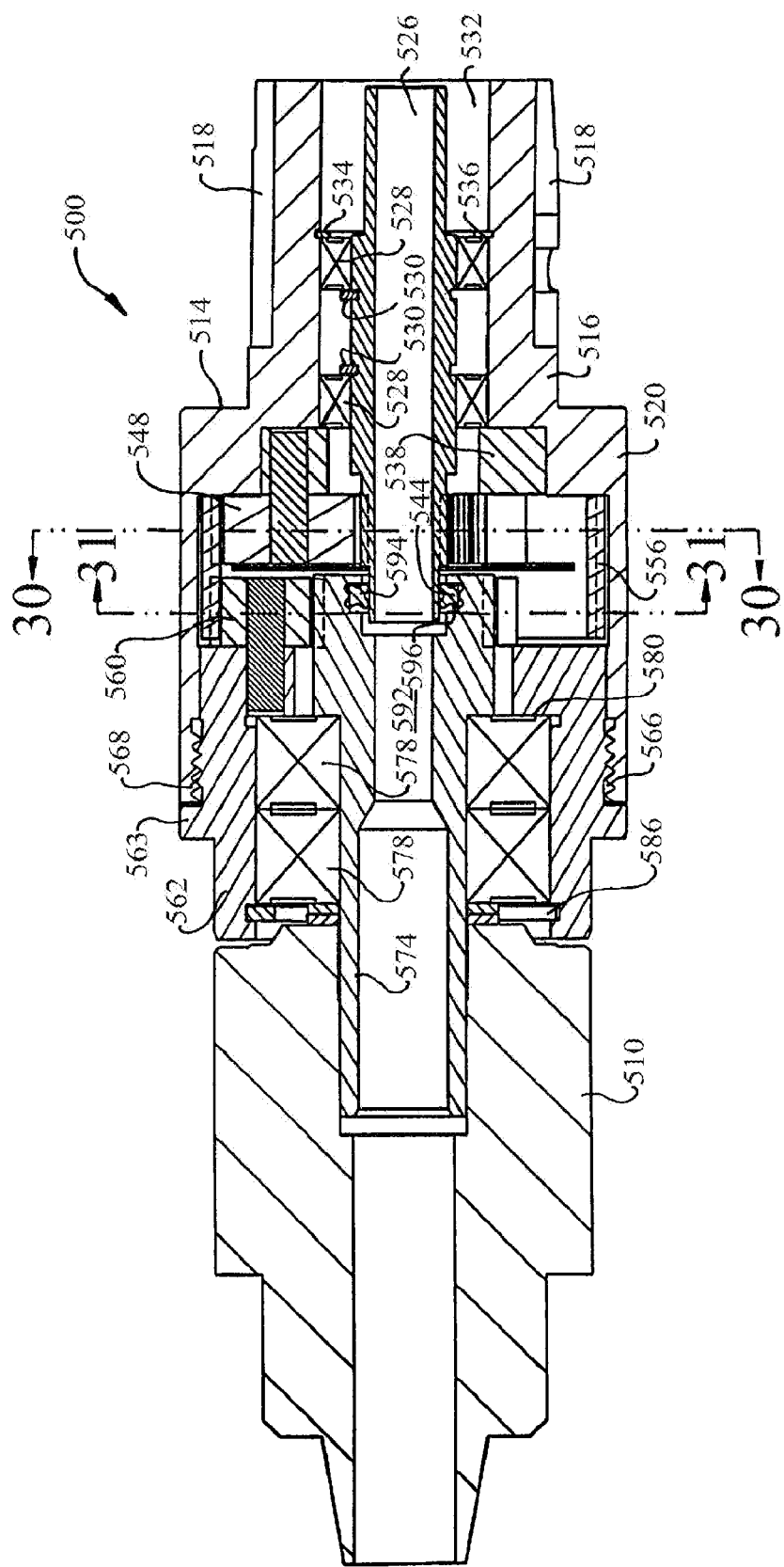
FIG. 29 is a longitudinal cross sectional view of the speed-altering surgical attachment.

Referring to FIGS. 28A and 29, the coupler may be implemented in the form of a speed-altering surgical attachment 500. The speed-altering surgical attachment 500 is operably engaged with the output member such that drive of the output member implemented in the form of an output drive shaft 574 causes drive of the speed-altering surgical attachment 500, which in turn actuates the surgical end effector 228 to perform an operational function. The speed-altering surgical attachment 500 alters the speed of the surgical end effector relative to the motor.

Referring to FIG. 28B, the speed-altering surgical attachment 500 includes a housing 502. An intermediate shaft 504 extends rearwardly from the housing 502. Intermediate shaft 504 is shaped to have a proximal end mounting head 506 with the same features as surgical end effector mounting head 234. Internal to the housing is a mounting assembly 508 represented by a phantom rectangle. Mount 508 is designed to releasably hold the proximal end of a surgical end effector (not illustrated) for rotation. The exact structure of the mount 508 is not relevant to this embodiment. Mount 508 may include the features of mounting assembly 226. Alternatively, mount 508 may be provided with features to hold mounting heads other than the described mounting head 234 for rotation. These include mounting heads with trinkle fittings, Hudson® fittings and modified trinkle fittings that are known in the surgical art.

Intermediate shaft 504 rotates mount 508. In this exemplary embodiment, intermediate shaft 504 and the spindle of mount 508 are the same component, and attachment 500 thus serves as a means for connecting a surgical end effector with a head different from mounting head 234 to the handheld surgical instrument. In this exemplary embodiment, the speed-altering surgical attachment rotates at the speed at which the handheld surgical instrument spindle 222 rotates. In other embodiments, such as the embodiment illustrated in FIG. 28A, there is a speed reducer or speed increaser gear assembly internal to the attachment housing 502 for transferring the rotational moment received by the input shaft 506 to the mounting head. The Applicants' Assignee's U.S. Pat. No. 5,993,454, DRILL ATTACHMENT FOR A SURGICAL DRILL, issued Nov. 30, 1999, and incorporated herein by reference in its entirety, shows one such assembly. This type of speed-altering surgical attachment may be provided with a spindle and mount substantially identical to the spindle 222 and mount 226 of the exemplary embodiment of the handheld surgical instrument.

The gear train and drive heads of this speed-altering surgical attachment may be of different design. For example, in some embodiments, the gear train may have three or more drive heads, each or which, in response to the single input rotational moment, operates at a different rotational speed. In some embodiments, the gear train has gears that cause one or more drive heads to rotate at speeds faster than those at which the motor output region 206 rotates.

The means by which the motor 204 rotates motor output region 206 may likewise vary from what has been described.

Similarly, the structure of the clutch 224 may differ from what has been described. For instance, some embodiments may have few or more laterally extending members, clutch pins, or other torque transmitting components, for simultaneously engaging a gear train drive head 266, 272 and the spindle 222. In some embodiments, clutch 224 may even include a single one of these members.

In some embodiments, the inner shifter and/or outer shifter may be arranged so that the points at which longitudinal motion are transferred to this sub assembly (indentions 374 in the described embodiment) are within the longitudinal slice in which the lateral member that transfers torque from one of the drive heads to the spindle is located. Such construction can further reduce the overall longitudinal length of the clutch.

Also, in some embodiments, the clutch pins may be integrally attached to the spindle. In these embodiments of the invention, the spindle itself is displaced in order to cause the clutch pins to engage the appropriate gear train drive head.

Similarly, in other embodiments, means other than a rotating shift ring may be employed to set the position of the clutch pins. In some embodiments, a switch member movably mounted to the handheld surgical instrument housing to move longitudinally is the surgeon-actuated component that is displaced to set the position of the clutch pins.

Also, the structure of the mounting assembly 226 and complementary speed-altering surgical attachment/surgical end effector mounting head may vary from what has been described. There is no requirement that in all embodiments the surfaces of the spindle that output torque and complementary mounting head boss 482 have a hexagonal or even a polygonal cross sectional profile. It is believed that a polygonal cross sectional geometry is the most efficient for ensuring torque transfer to the mounting head.

Similarly, the mounting head body 484 may have a geometry different from what has been described and illustrated. There is no requirement that in all embodiments this component and the complementary spindle bore have circular cross-sectional profiles. In some embodiments, these components may even have one or more planar faces. It is believed though such geometry is an optimal geometry for reducing mounting head wobble. Similarly, there is no requirement that in all embodiments of the invention, the indentation defined by the mounting head body for receiving the locking member associated with the handheld surgical instrument mounting assembly be an annular groove. In some embodiments, one or more indentations are provided in the mounting head body for receiving the complementary locking member integral with the complementary handheld surgical instrument mounting assembly.

In some embodiments, the mounting body may not have any geometric features for receiving complementary mounting assembly locking members. Also, there may be embodiments wherein the geometric features for facilitating the engagement of the handheld surgical instrument mount with the mounting head project beyond the surface of the mounting head body.

Similarly, there may be embodiments in which the mounting head body has a diameter that is identical with that of the distally adjacent speed-altering surgical attachment/surgical end effector shaft. In still other embodiments, the surgical attachment/surgical end effector shaft may have a diameter greater than that of the mounting head.

Likewise, an surgical attachment/surgical end effector mounting head of this embodiment may be constructed with geometric features different from slots 488 and beveled faces 492 to facilitate the alignment of the mounting head in the spindle bore. Some embodiments may not even be provided with any of these features.

Other mounts may, instead of holding a speed-altering surgical attachment/surgical end effector mounting head to the spindle, serve only to cause the mounting head to be driven by the spindle. Moreover, manufacturers of handheld surgical instruments often provide removable speed-altering surgical attachments for mounting to handheld surgical instruments that have their own speed reduction gear assemblies. The ability to selectively couple a speed-altering surgical attachment to a surgical tool makes it possible for a surgeon to even further increase the torque available to the cutting tool coupled to the handheld surgical instrument. Often, these speed-altering surgical attachments are designed to reduce the speed and increase the torque by a pre-set whole number ratio. For example, speed-altering surgical attachments with internal gear assemblies that decrease speed of the motor drive shaft by 3:1 or 4:1 have been provided. (It should be understood that the above ratio refers to the relationship of the input shaft speed to the output shaft speed. The reciprocal of these ratios give the relationship between torque input and torque output.)

Moreover, manufacturers of handheld surgical instruments often provide removable speed-altering surgical attachments for mounting to handheld surgical instruments that have their own speed reduction gear assemblies. The ability to selectively couple a speed-altering surgical attachment to a surgical tool makes it possible for a surgeon to even further increase the torque available to the surgical end effector coupled to the handheld surgical instrument. Often these speed-altering surgical attachments are designed to reduce the speed/increase the torque by a pre-set whole number ratio. For example, speed-altering surgical attachments with internal gear assemblies that decrease speed of the motor drive shaft by 3:1 or 4:1 have been provided. It should be understood that the above ratios refer to the relationship of the input shaft speed to the output shaft speed. The reciprocal of these ratios gives the relationship between torque input and torque output.

Referring to FIG. 29, one embodiment of an attachment gear assembly 500 is intended for use with a handheld surgical instrument for increasing the torque of the surgical end effector attached to the handheld surgical instrument. The gear assembly can be used to obtain a 2:1 reduction of motor speed wherein the output force is both centered around the axis around which the input force is applied and in the same direction as the direction of the input force.

Figure 32:
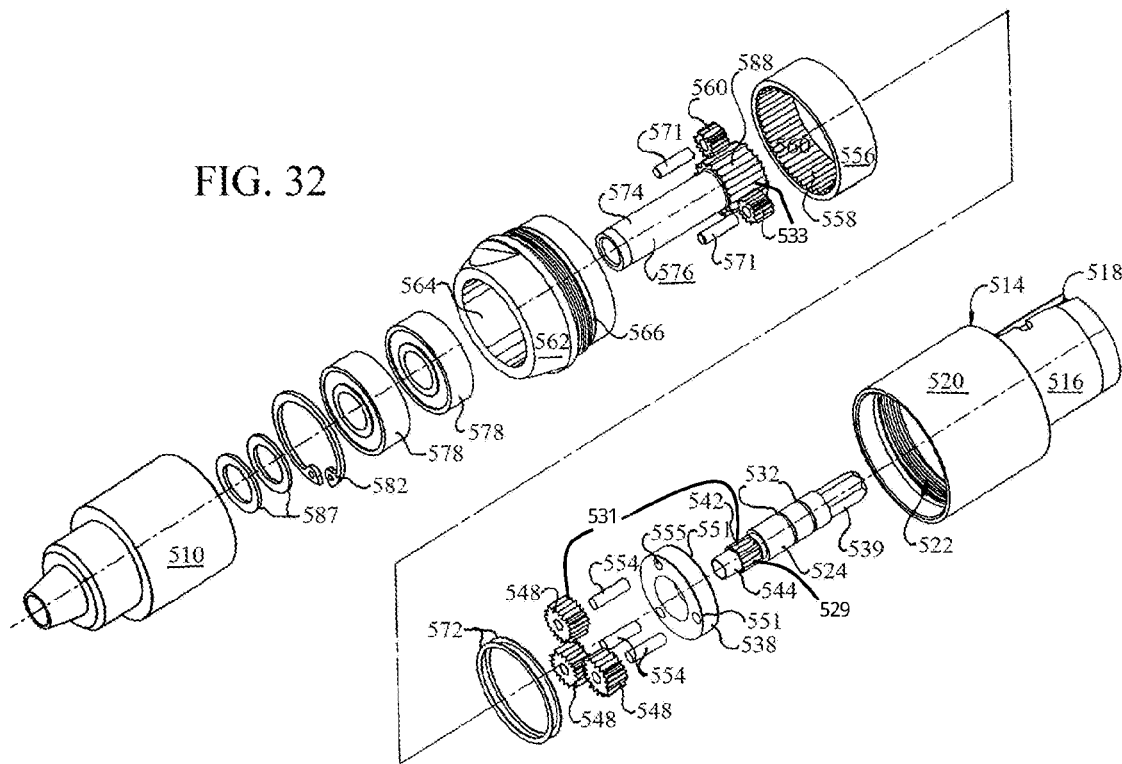
FIG. 32 is an exploded view of the speed-altering surgical attachment.
Figure 33:
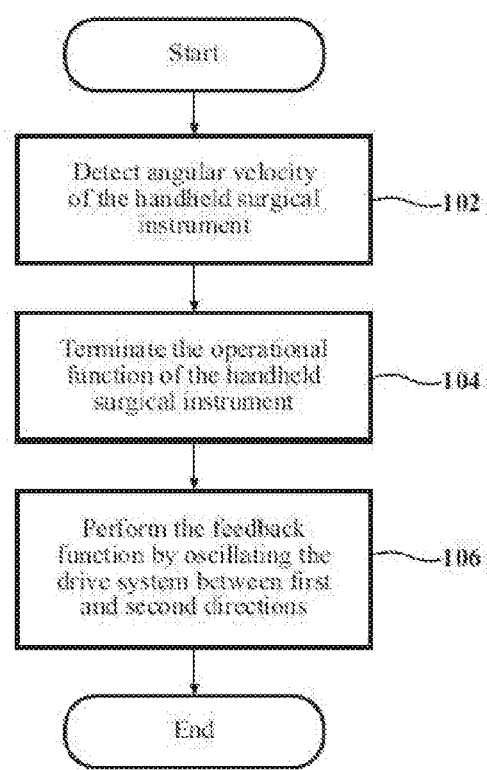
FIG. 33 is a flow chart for a method of method for providing feedback to a user of a handheld surgical instrument.

Referring to FIGS. 28A and 32, the speed-altering surgical attachment 500 comprises an intermediate shaft 524 defining a shaft input region 528 operably coupled to an output member implemented in the form of a spindle 222 such that drive of the spindle 222 is configured to cause drive of the shaft input region 528. The intermediate shaft 524 further defines a shaft output region 529. A gear train 530 defines a gear train input region 531 operably coupled to the shaft output region 529 such that drive of the shaft output region 529 is configured to cause drive of the gear train input region 531. The gear train 530 further defines a gear train output region 533 operably coupled to the gear train input region 531 and the surgical end effector 228 such that drive of the gear train input region 531 is configured to cause drive of the gear train output region 533 and actuation of the surgical end effector 228.

Figure 30:
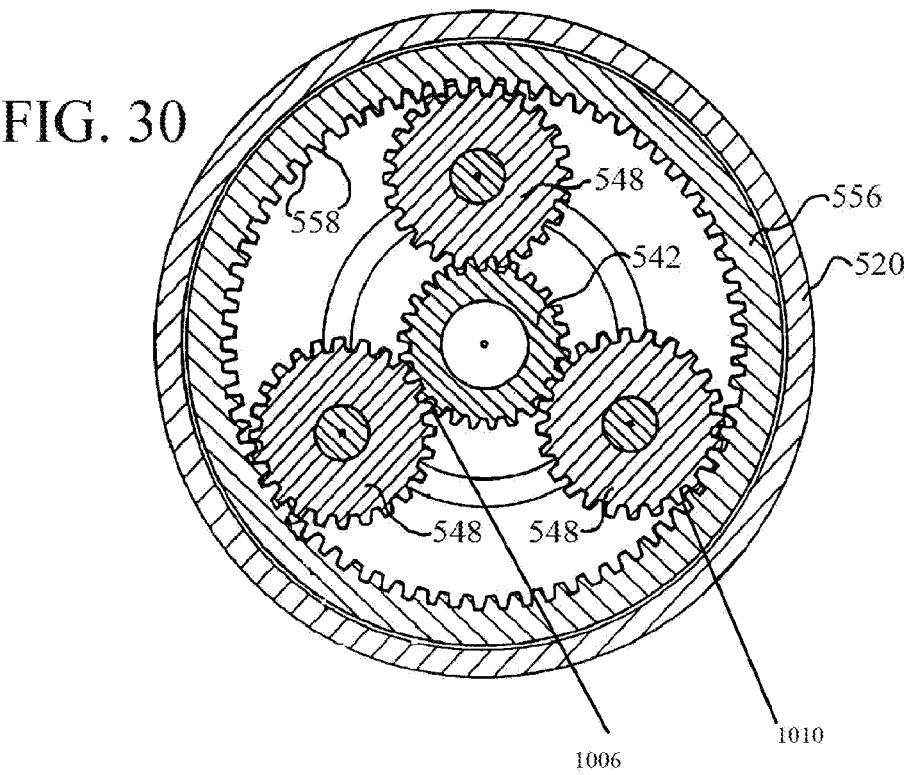
FIG. 30 is a lateral cross sectional view of the input gear train of the speed-altering surgical attachment of FIG. 29 taken along line 30-30.

The shaft output region 529 of the intermediate shaft 524 interfaces with the gear train input region 531 at shaft-gear train interface 1006, and the shaft-gear train interface 1006 comprises a shaft-gear train backlash such that drive of the shaft output region 529 within the shaft-gear train backlash does not cause drive of the gear train input region 531. In this embodiment, the gear train input region 529 may be implemented in the form of planet gears 548 coupled to the shaft output region, which may be implemented in the form of an input sun gear 542 (as shown in FIG. 30). The gear train output region 533 may comprise an output sun gear 588 operably coupled to the planet gears 560 and the surgical end effector 228 (as shown in FIG. 27) such that drive of the planet gears 560 is configured to cause drive of the output sun gear 588 and actuation of the surgical end effector 228.

Referring to FIG. 28A, the shaft output region 529 interfaces with the gear train input region 531 at a shaft-gear train interface having shaft-gear train backlash 1006 (as shown in FIG. 28A) such that drive of the shaft output region 529 within the shaft-gear train backlash 1006 does not cause drive of the gear train input region 531.

The speed-altering surgical attachment 500 is mounted to the front end of the handheld surgical instrument 200 so as to seat in a collar integral with the front of the hand held surgical instrument. The gear train 530 internal to the speed-altering surgical attachment 500 transfers the rotational power developed by shaft 532 to a chuck 510 mounted to the front of the speed-altering surgical attachment. Chuck 510 may be used to hold the surgical end effector 228. In the depicted embodiment, the surgical end effector 228 is a drill bit.

Referring to FIGS. 29 to 32, the speed-altering surgical attachment 500 includes an input housing 514 which contains most of the components of the attachment. Input Housing 514 is formed to have a narrow diameter stem section 516. Stem section 516 is the portion of the housing 514 that is inserted into the handheld surgical instrument 200. The outer surface of stem 516 is formed to attach the speed-altering surgical attachment 500 to the handheld surgical instrument, an anti-rotation key that stops movement of the attachment (key not illustrated). Input housing 514 is further formed to have a head 520 that is integral with and extends coaxially forward from stem 516. In the depicted embodiment, head 520 has an outer diameter greater than that of stem 516. A multi-section bore 522 extends through input housing 514 from the end of the stem 516 coupled to handheld surgical instrument 200 to the front end of the head 520.

The intermediate shaft 524 is rotatably mounted in the portion of housing bore 522 that extends from the open end of the housing stem 516 to the portion of the head 520 adjacent the stem. Two spaced apart bearing assemblies 528 rotatably connect intermediate shaft 524 to input housing 514.

The intermediate shaft 524 is formed with a bore 526 that extends axially through the intermediate shaft. Intermediate shaft 524 is further formed to have an end 539 (as shown in FIG. 32), closest to handheld surgical instrument 200 that is shaped to have a polygonal shaped outer surface. When the speed-altering surgical attachment 500 is coupled to a handheld surgical instrument 200, the drive shaft end 539 seats in a complementary-profiled opening formed in the head of spindle 222 (as shown in FIG. 6B). Consequently, the rotation of spindle 222 causes a like rotation of intermediate shaft 524.

Intermediate shaft 524 is formed to have a head provided with gear teeth that form an input sun gear 542. The intermediate shaft 524 also has a nose section 544 located forward of the input sun gear 542. The outer diameter of nose section 544 is less than the outer diameter of the input sun gear 542.

The input sun gear 542 engages three input planet gears 548 that are rotatably mounted to the input housing 514. More specifically, the input planet gears 548, which are uniformly spaced about the longitudinal axis of intermediate shaft 524, are mounted to the planet carrier 538. The planet carrier 538 is ring-shaped and located around intermediate shaft 524. Planet carrier 538 is press fit in a stepped section of housing bore 522 located in the portion of the head 520 of the housing adjacent stem 516. In the depicted embodiment of the invention, the forward and rear outer edges of planet carrier 538 are formed with inwardly directed steps 551 to facilitate the mounting of the carrier in input housing 514. Each of the input planet gears 548 is rotatably mounted to fixed axle pin 554. Axle pins 554 are press fit in bores 555 that extend through planet carrier 538.

A circularly shaped ring gear 556 surrounds the input planet gears 548. Ring gear 556 has an inner surface with teeth 558 that engage input planet gears 548. The outer wall of ring gear 556 is smooth. Ring gear 556 is further designed so that its outer diameter is less than the diameter of the adjacent inner wall of input housing 514 that defines the section of the housing bore 522 in which the ring gear is seated. Thus, there is a small interstitial space between the outer wall of the ring gear 556 and the adjacent inner wall of the input housing 514. In some embodiments, the gap between the inner wall of the input housing 514 and the outer wall of the ring gear 512 is approximately between 0.007 and 0.011 inches (0.18 and 0.28 mm). Thus, ring gear 556 "floats" relative to input housing 514.

The gear assembly of this embodiment includes a second set of planet gears or output planet gears 560 that also engage ring gear 556. The output planet gears 560 are fitted to an output housing 562 that is mounted in and extends forward from the open end of input housing head 520. The output housing 562 is a generally ring-shaped structure with a bore 564 that extends axially through it. Output housing bore 564 extends coaxially with input housing bore 522. The rear end of output housing 562 is seated in the front end of the input housing bore 522. The outer surface of the middle section of output housing 562 is provided with threading 566. The threading 566 engages threading 568 provided around the inner wall of input housing 514. The output housing 562 is further formed to have an outwardly extending annular lip 563 located forward of the surface on which threading 566 is formed. Lip 563 extends over the open forward end of input housing 514 to limit the extent to which the output housing 562 is seated in input housing bore 522.

The output planet gears 560 are seated against the rearwardly directed face of output housing 562. The output planet gears 560 are rotatably mounted over fixed axle pins 571. The axle pins 571 are press fit into bores (not identified) that extend into the output housing 562 from the rearwardly directed face of the housing 562. It will be further noted that, within the ring gear 556, two ring-shaped washers 572 are located between input and output planet gears 548 and 560, respectively. Washers 572 are provided to prevent the output planet gears 560 from separating from the output housing 562.

An output drive shaft 574 is located in output housing bore 564. The output drive shaft 574 has an elongated stem section 576 that extends out of the front end of the output housing 562. Two bearing assemblies 578 that extend between the inner wall of the output housing 562 that defines bore 564 and the stem section 576 rotatably mount the output drive shaft 574 in the output housing 562. The rear face of the rearward of the two bearing assemblies 578 abuts an inwardly directed step 580 internal to output housing 562. A retaining ring 582 prevents the bearings from coming out of the front end of output housing bore 564. The outer perimeter of retaining ring 582 is seated in an annular groove 586 formed in the inner wall of output housing 562 that defines bore 564. Two washers 587 are located between the front face of the forward-most bearing assembly 578 and the adjacent surface of chuck 510.

The output drive shaft 574 has a toothed head that functions as an output sun gear 588. Output sun gear 588 is shaped to have a diameter greater than that of the stem 576 with which it is integrally formed. Owing to its large diameter, output sun gear 588 blocks outward movement of the input planet gears 548 so as to prevent the input planet gears from coming out of the planet carrier 538.

It will also be noted that, in the illustrated embodiment, output drive shaft 574 has a bore 592 that extends axially through the shaft. From FIG. 29 it can be seen that the nose section 544 of intermediate shaft 524 extends into the adjacent open end of bore 592 of output drive shaft 574. A flexible quad ring 594 is seated in an annular groove 596 formed contiguously with bore 592 inside output drive shaft 574. Quad ring 594 is fitted over the portion of the nose section 544 that extends into bore 592. The quad ring 594 provides a barrier to prevent lubricating material disposed inside the gear assembly from flowing outside the speed-altering surgical attachment 500 along the inner walls of either the intermediate shaft 506, 524 or the output drive shaft 574.

The output drive shaft 574 engages chuck 510. Internal to the embodiment of the chuck are jaws that hold the surgical end effector 228 in place. (The jaws and other components internal to the chuck 510 are not illustrated.) One type of chuck 510 integral with speed-altering surgical attachment 500 is a "Jacobs" chuck. The jaws rotate in unison with the output drive shaft 574 so as to cause a like movement of the surgical end effector 228.

The gear train 530 comprises a plurality of gears meshed with one another at a plurality of internal gear train interfaces, and at least one of the internal gear train interfaces comprises an internal gear train backlash such that drive of the gear train input region within the internal gear train backlash does not cause the surgical end effector to perform the operational function.

Figure 31:
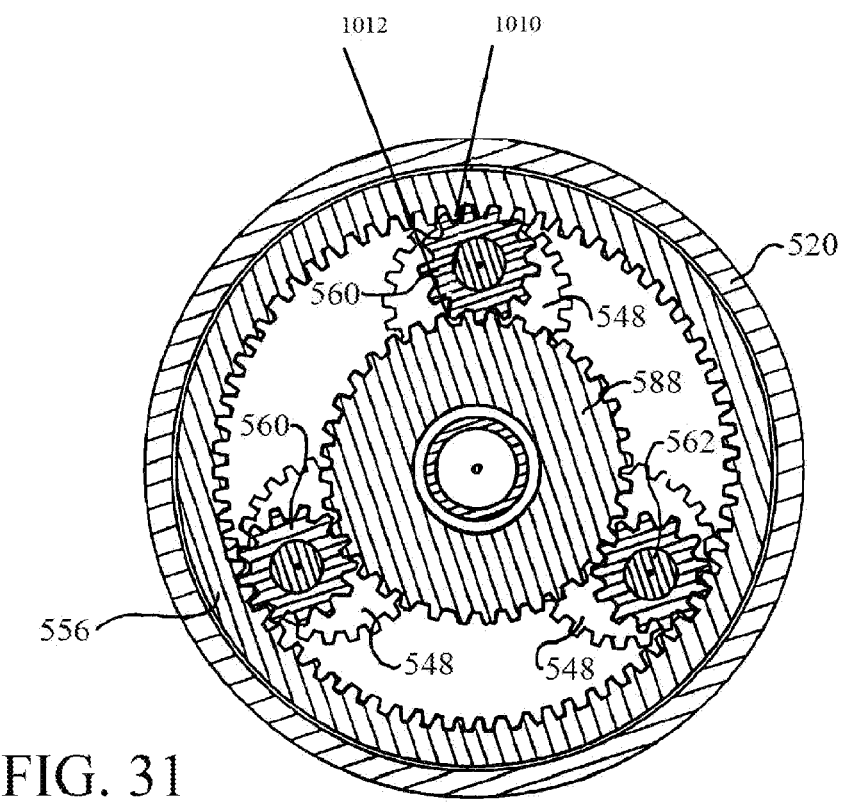
FIG. 31 is a lateral cross sectional view of the output gear assembly of the speed-altering surgical attachment of FIG. 29 taken along line 31-31.

The gear train 530 comprises a plurality of gears 542, 548, 556, 560, and 588 meshed with one another at a plurality of internal gear interfaces 1006, 1010, 1012 (as shown in FIGS. 30 and 31), and at least one of the internal gear train interfaces comprises an internal gear train backlash such that drive of the gear train input region within the internal gear train backlash does not cause the surgical end effector to perform the operational function.

Referring to FIG. 28A, when the handheld surgical instrument 200 is actuated, the rotation of the output member comprising spindle 222 causes the intermediate shaft 524 to rotate. The movement of the intermediate shaft 524 and the input sun gear 542 integral therewith causes the input planet gears 548 to rotate around their axes. The rotation of the input planet gears 548 causes the ring gear 556, which is not fixed, to rotate. Actuation of the ring gear 556, in turn, forces the output planet gears 560 to rotate around their axes. The movement of the output planet gears 560 forces the rotation of the output sun gear 588 and output drive shaft 574. The rotation of the output drive shaft causes the like movement of the surgical end effector 228 coupled to it by the chuck 510.

It should be recognized that the foregoing description is directed to specific embodiment and that other embodiments may vary from what has been described. For example, there is no requirement that the speed-altering surgical attachment comprise input and output drive shafts dimensioned to cause a 2:1 reduction between input and output rotational speeds. In other embodiments, the drive shafts 524, 574 can be dimensioned to cause the output drive shaft to spin faster than the intermediate shaft. Moreover, the components from which the speed-altering surgical attachment are assembled may vary from what has been described. For example, in some embodiments the input planet gears may be directly mounted to the housing in which the planet gears are contained. Still other embodiments may have a single housing.

Also, there is no requirement that the axes along which the input and output planet gears 548, 560, respectively, rotate lie along a common radial line that extends outward from the center of the speed-altering surgical attachment 500. While this alignment is depicted in FIG. 29, it is not required in all embodiments. Moreover, there need not always be a 1:1 ratio in the number of input planet gears to the number of output planet gears.

Also, only one particular type of mount was shown in association with the handheld surgical instrument for holding a complementary surgical end effector. It is contemplated that other mounts may be used with this speed-altering surgical attachment.

It should likewise be recognized that, some embodiments of the speed-altering surgical attachment 500 may be permanently fitted to the handheld surgical instrument 200. Also, the term surgical end effector should be understood to encompass other forms of surgical tools such as burs and wire drivers.

FIGS. 5B, 28A, 30, and 31 illustrate the different interfaces that may have backlash when the coupler is implemented in the form of a speed-altering surgical attachment. Interface 1000 (as shown FIG. 5B) between the motor output region 251 and the transmission input region 242 may have backlash. Interface 1002 (as shown in FIG. 28A) between internal gears of the transmission may have backlash. Interface between gear sets 252, 254 may have backlash. Interface between gear sets 256, 262 may have backlash.

FIGS. 28A, 30, and 31 depicts an exemplary embodiment of backlash at interfaces 1006, 1010, 1012 within a speed-altering surgical attachment 500 affixed to a handheld surgical instrument 200. It is contemplated that movement of the motor within the cumulative backlash for all interfaces between driving components of the handheld surgical instrument can provide a feedback function while not driving the surgical end effector and performing the operational function.

FIG. 30 is a view of interface 1006 between sun gear 542 and planet gears 548 (only one of the three points referenced) having backlash. FIG. 30 also shows interface 1010 between the planet gears 548 and the ring gear 556 (only one of three points referenced) having backlash. FIG. 31 shows interface 1010 between the ring gear 556 and the output planet gears 560 (only one of three points referenced) having backlash. Interface 1012 between the output planet gears 560 and the output sun gear 588 (only one of three points referenced) has backlash. It should be recognized that the foregoing description is directed to specific embodiments and that other embodiments may vary from what has been described. It is contemplated that oscillating the drive system 18 between the first and second directions for the feedback signal FS will fall less than the cumulative backlash starting from the motor-transmission interface 1000 through the last possible interface before the surgical end effector 228, which will be embodiment specific.

Referring to FIG. 35, a method 100 for providing feedback to a user of the handheld surgical instrument 10 of FIGS. 1-4C is illustrated. The method 100 commences at step 102 with the step of detecting a grip event. In particular, the gyroscope 36 may detect the angular velocity of the handheld surgical instrument 10, and the current sensor 38 may detect that the input device 22 was actuated to supply current from the battery 50 to the drive system 18. However, the handheld surgical instrument can comprise one, three, four, or more sensors of any suitable type for detecting any condition associated with the grip event.

At step 104, the operational function OF of the handheld surgical instrument 10 may be terminated when the grip event is detected. In particular, the controller 20 may receive the first and second grip event signals ES1, ES2 from the gyroscope 36 and current sensor 38. The controller 20 may determine that the grip event occurred when the controller 20 determines that the first grip event signal ES1 indicates that the handheld surgical instrument is being rotated by the predetermined threshold angular velocity, e.g., 500 degrees per second, and the second signal ES2 generated by the current sensor 38 indicates that current is being supplied to the drive system 18. In other examples, the controller 20 may determine that a grip event has occurred in response to receiving other signals from any suitable sensor indicating that one or more thresholds associated with a grip event have been satisfied.

When the controller determines that the grip event has occurred, the controller 20 may terminate the operational function OF of the surgical end effector 12 by stopping the output member 16. For example, the controller 20 may terminate sending the operate signal OS to the drive system 18 in order to stop the binding, pinching, or misalignment that is impeding rotation or other cutting motion of the surgical end effector 12. In other embodiments, the controller 20 may further terminate the operational function OF by actuating a braking device (not shown) to stop or slow movement of the surgical end effector 12.

At step 106, the controller 20 may control the drive system 18 upon detection of the grip event to perform the feedback function by oscillating the drive system 18 between the first and second directions, without moving the surgical end effector 12 and causing the surgical end effector 12 to perform the operational function OF. More specifically, the controller 20 may actuate one or more components of the motor 24 or the transmission 26 to oscillate within the tolerances between surfaces that engage one another such that the oscillation of one component does not move the other component and the coupler 14.

This method allows the user to know that the drill stopped moving because of a kickback event. By having a different modality of indication between a status of the battery and kickback events, confusion is eliminated. This is because visual indicators on batteries may often be used to communicate status on the battery. If the same visual indicator were to be used to indicate the triggering of an anti-kickback event, the user may be confused as to whether the battery status stopped the device from operating or the kickback event stopped the device from operating.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described. It will be further appreciated that the terms "include," "includes," and "including" have the same meaning as the terms "comprise," "comprises," and "comprising."

Embodiments of the disclosure can be described with reference to the following numbered clauses, with specific features laid out in the dependent clauses:

I. A handheld surgical instrument to provide tactile feedback to a user during a kickback event, the handheld surgical instrument comprising:
    an input device configured to generate an input signal;
    a drive system;
    a coupler configured to receive a surgical end effector, said coupler operably engaged with said drive system;
    said drive system configured to perform:
        an operational function, and
        a feedback function, separate from said operational function, to provide feedback to a user; and
    a controller in communication with said drive system and said input device, said controller configured to control said drive system to perform said operational function in response to receiving said input signal from said input device, and said controller configured to oscillate said output member to perform a feedback function while not causing the surgical end effector to perform an operational function.

II. The handheld surgical instrument of clause I wherein said controller is configured to terminate said operational function of said drive system when said drive system performs said feedback function.

III. The handheld surgical instrument of any one of clauses I or II further comprising:
    a gyroscope configured to detect movement of the handheld surgical instrument and generate a first grip event signal based on the movement of the handheld surgical instrument being associated with a grip event; and
    a current sensor configured to detect a supply current to said drive system and generate a second grip event signal based on said supply current being associated with the grip event;
    said controller generating a feedback signal when said controller receives said first and second grip.

IV. The handheld surgical instrument of any one of clauses I, II, or III wherein said gyroscope is configured to detect rotation of the handheld surgical instrument at a rate of at least 500 degrees per second.

V. A method for providing feedback to a user of a handheld surgical instrument comprising a drive system, a coupler operably engaged with the drive system, a surgical end effector operably engaged with the coupler to perform an operational function, a first sensor configured to generate at least one grip event signal, and a controller communicating with the first sensor and the drive system, the method comprising the steps of:
 detecting a grip event based on the at least one grip event signal;
 terminating the operational function of the handheld surgical instrument when said grip event is detected; and
 controlling the drive system, with the controller, to oscillate the drive system in first and second directions, without causing the surgical end effector to perform the operational function, upon detection of the grip event.

VI. The method of clause V further comprising actuating said drive system to perform said feedback function while not actuating the surgical end effector to perform said operational function.

VII. A method for providing feedback to a user of a handheld surgical instrument comprising a drive system, a coupler operably engaged with the drive system, a surgical end effector operably engaged with the coupler, a first sensor configured to generate at least one grip event signal, and a controller communicating with the first sensor and the drive system, the method comprising the steps of:
 detecting a grip event based on the at least one grip event signal; and
 generating tactile feedback upon detection of the grip event.

VIII. A method for providing feedback to a user of a handheld surgical instrument comprising a drive system, a coupler operably engaged with the drive system, a removable battery coupled to the handheld surgical instrument, a surgical end effector operably engaged with the coupler, a first sensor configured to generate at least one grip event signal, and a controller communicating with the first sensor and the drive system, the method comprising the steps of:
 detecting a grip event based on the at least one grip event signal;
 generating tactile feedback upon detection of the grip event; and
 generating a visual indicator based on the status of the removable battery.

What is claimed is:

1. A handheld surgical instrument configured to provide tactile feedback in the event of kickback, comprising:
 a rotary surgical end effector;
 a coupler configured to operably couple to said rotary surgical end effector to cause rotation of said rotary surgical end effector;
 a motor comprising a motor shaft defining a motor output region, said motor configured to drive said motor output region; and
 a transmission defining a transmission input region that interfaces with said motor output region, said transmission further defining a transmission output region coupled to said transmission input region, said transmission output region being operably coupled to said coupler, said transmission configured to alter a speed of said coupler relative to said motor output region;
 wherein said motor output region and said transmission input region interface one another at a motor-transmission interface, and said motor-transmission interface having a motor-transmission backlash such that drive of said motor output region within said motor-transmission backlash does not cause rotation of said rotary surgical end effector;
 a sensor configured to generate a grip event signal; and
 a controller operably engaged with said sensor to receive said grip event signal from said sensor, and said controller is configured to determine a grip event based on said grip event signal;
 wherein said controller is configured to oscillate said motor shaft to perform a feedback function without rotating said rotary surgical end effector.

2. The handheld surgical instrument of claim 1 wherein said grip event comprises said surgical end effector becoming bound, pinched, or misaligned while said surgical end effector is being actuated for performing an operational function such that debris impedes a motion of the surgical end effector and kickback transfers torque from the surgical end effector through said transmission and said motor to a user.

3. The handheld surgical instrument of claim 1, wherein said coupler is in a form of a speed-altering surgical attachment operably engaged with said transmission for actuating said surgical end effector to perform an operational function and altering a speed of said surgical end effector relative to said motor.

4. A handheld surgical instrument to provide tactile feedback to a user during a kickback event, the handheld surgical instrument comprising:
 a coupler configured to operably couple to a surgical end effector;
 a drive system comprising an output member operably engaged with said coupler for actuating said surgical end effector to perform an operational function;
 a first sensor configured to generate a grip event signal; and
 a controller operably engaged with said first sensor to receive said grip event signal from said first sensor, and said controller is configured to determine a grip event based on said grip event signal;
 wherein said controller is further configured to oscillate said drive system in first and second directions to perform a feedback function while not causing the surgical end effector to perform said operational function.

5. The handheld surgical instrument of claim 4 wherein said grip event comprises said surgical end effector becoming bound, pinched, or misaligned while said surgical end effector is being actuated for performing an operational function such that debris impedes a motion of the surgical end effector and kickback transfers torque from the surgical end effector through a transmission and a motor of the drive system to the user.

6. The handheld surgical instrument of claim 4, wherein said controller is configured to terminate said operational function of said surgical end effector by stopping said output member when said controller determines said grip event based on said grip event signal.

7. The handheld surgical instrument of claim 4, further comprising a second sensor, wherein said first sensor comprises:
 a gyroscope configured to detect movement of the handheld surgical instrument indicative of said grip event; and
 said second sensor comprises a current sensor configured to detect a supply current associated with said grip event.

8. The handheld surgical instrument of claim 4 wherein said first sensor comprises a gyroscope configured to detect rotation of the handheld surgical instrument at a rate of at least 500 degrees per second.

9. The handheld surgical instrument of claim 4 wherein the drive system includes a transmission comprising a plurality of gears meshed with one another at a plurality of internal transmission interfaces, and at least one of said internal transmission interfaces comprises an internal transmission backlash.

10. The handheld surgical instrument of claim 9 wherein said transmission comprises a planetary gear train that defines a plurality of stages interfacing with one another at a plurality of internal transmission interfaces, and at least one of said plurality of internal transmission interfaces comprises an internal transmission backlash such that drive of said transmission within said internal transmission backlash does not cause drive of said output member.

11. The handheld surgical instrument of claim 4 wherein said drive system comprises:
 a motor comprising a motor shaft defining a motor output region, said motor configured to drive said motor output region; and
 a transmission defining a transmission input region operably coupled to said motor output region such that said motor output region is configured to cause drive of said transmission input region, said transmission further defining a transmission output region operably coupled to said transmission input region such that drive of said transmission input region is configured to cause drive of said transmission output region, said transmission output region being operably coupled to said output member such that drive of said transmission output region is configured to cause drive of said output member and alter a speed of said output member relative to said motor;
 wherein said motor output region and said transmission input region interface one another at a motor-transmission interface, said motor-transmission interface having a motor-transmission backlash such that drive of said motor output region within said motor-transmission backlash does not cause drive of said transmission input region.

12. The handheld surgical instrument of claim 11 further comprising a clutch defining a clutch input region that is operably coupled to said transmission output region such that drive of said transmission output region is configured to cause drive of said clutch input region, and said clutch further defining a clutch output region operably coupled to said output member;
 wherein said transmission output region and said clutch input region interface one another in at least one transmission-clutch interface having a transmission-clutch backlash such that drive of said transmission output region within said transmission-clutch backlash does not cause drive of said clutch input region.

13. The handheld surgical instrument of claim 11 wherein said transmission output region comprises two gear sets, and the handheld surgical instrument further comprises a clutch defining a clutch input region, said clutch input region being movable to a first position where one of the two gear sets is operably coupled to the clutch input region and configured to cause drive of said clutch input region, said clutch input region further being movable to a second position where the other one of the two gear sets is operably coupled to said clutch input region and configured to cause drive of said clutch input region, and said clutch further defining a clutch output region operably coupled to said output member;
 said clutch in said first position being configured to interface said clutch input region with one of said two gear sets at a first transmission-clutch interface having a first transmission-clutch backlash such that drive of said transmission output region within the first transmission-clutch backlash does not cause drive of said clutch input region; and
 said clutch in said second position being configured to interface said clutch input region with the other one of said two gear sets at a second transmission-clutch interface having a second transmission-clutch backlash such that drive of said transmission output region within the second transmission-clutch backlash does not cause drive of said clutch input region.

14. The handheld surgical instrument of claim 11, wherein said coupler is in the form of a speed-altering surgical attachment operably engaged with said output member for actuating a surgical end effector to perform an operational function and altering a speed of said surgical end effector relative to said motor.

15. The handheld surgical instrument of claim 14, wherein said speed-altering surgical attachment comprises:
 an intermediate shaft defining a shaft input region operably coupled to said output member such that drive of said output member is configured to cause drive of said shaft input region, and said intermediate shaft further defines a shaft output region;
 a gear train defining a gear train input region operably coupled to said shaft output region such that drive of said shaft output region is configured to cause drive of said gear train input region, said gear train further defining a gear train output region operably coupled to said gear train input region and said surgical end effector such that drive of said gear train input region is configured to cause drive of said gear train output region and actuation of said surgical end effector;
 wherein said shaft output region of said intermediate shaft interfaces with said gear train input region at shaft-gear train interface, and said shaft-gear train interface comprises a shaft-gear train backlash such that drive of said shaft output region within said shaft-gear train backlash does not cause drive of said gear train input region.

16. The handheld surgical instrument of claim 15, wherein said gear train comprises a plurality of gears meshed with one another at a plurality of internal gear train interfaces, and at least one of said internal gear train interfaces comprises an internal gear train backlash such that drive of said gear train input region within said internal gear train backlash does not cause the surgical end effector to perform the operational function.

17. The handheld surgical instrument of claim 4, further comprising a visual indicator, said controller is further configured to actuate said visual indicator when said controller determines a grip event based on said grip event signal.

18. The handheld surgical instrument of claim 17 wherein said visual indicator comprises a light emitter.

19. The handheld surgical instrument of claim 17 wherein said visual indicator comprises a ring-shaped light guide.

20. The handheld surgical instrument of claim 17, further comprising a battery, with said battery comprising said visual indicator.

21. A method for providing feedback to a user of a handheld surgical instrument comprising a drive system having backlash, a coupler operably engaged with the drive system, a surgical end effector operably engaged with the coupler to perform an operational function, a first sensor configured to generate at least one grip event signal, and a controller communicating with the first sensor and the drive system, the method comprising the steps of:

detecting a grip event based on the at least one grip event signal; and oscillating the drive system within the backlash without rotating or oscillating the surgical end effector upon detection of the grip event.

* * * * *